US008892215B2

(12) United States Patent
Lipani

(10) Patent No.: US 8,892,215 B2
(45) Date of Patent: Nov. 18, 2014

(54) SYSTEM AND METHOD FOR ELECTRICAL STIMULATION OF THE LUMBAR VERTEBRAL COLUMN

(71) Applicant: John D. Lipani, New Hope, PA (US)

(72) Inventor: John D. Lipani, New Hope, PA (US)

(*) Notice: Subject to any disclaimer, the term of this patent is extended or adjusted under 35 U.S.C. 154(b) by 0 days.

(21) Appl. No.: 14/099,910

(22) Filed: Dec. 7, 2013

(65) Prior Publication Data

US 2014/0135876 A1 May 15, 2014

Related U.S. Application Data

(62) Division of application No. 13/402,093, filed on Feb. 22, 2012.

(51) Int. Cl.
A61N 1/28 (2006.01)
A61N 1/36 (2006.01)
A61B 18/14 (2006.01)
A61N 1/20 (2006.01)
A61N 1/05 (2006.01)
A61B 18/00 (2006.01)

(52) U.S. Cl.
CPC ............ A61N 1/205 (2013.01); A61N 1/36171 (2013.01); A61B 2018/0044 (2013.01); A61N 1/36057 (2013.01); A61N 1/36178 (2013.01); A61B 18/1492 (2013.01); A61N 1/0551 (2013.01); A61B 2018/00613 (2013.01); A61N 1/36071 (2013.01)
USPC ................. 607/117; 607/118; 607/3; 607/98; 607/102

(58) Field of Classification Search
USPC ................................ 607/3, 98, 102, 117, 118
See application file for complete search history.

(56) References Cited

U.S. PATENT DOCUMENTS

| 3,727,616 | A | 4/1973 | Lenzkes |
| 4,633,889 | A | 1/1987 | Talalla |
| 6,249,703 | B1 | 6/2001 | Stanton |
| 6,622,048 | B1 | 9/2003 | Mann |
| 6,654,644 | B2 | 11/2003 | Sanchez-Zambrano |
| 6,772,012 | B2 | 8/2004 | Ricart |
| 6,830,570 | B1 | 12/2004 | Frey |
| 7,069,083 | B2 | 6/2006 | Finch |
| 7,270,659 | B2 | 9/2007 | Ricart |

(Continued)

OTHER PUBLICATIONS

Humzah MD, Soames RW. Human intervertebral disc: structure and function. Anat Rec 220(4,1988):337-356.

(Continued)

Primary Examiner — Christopher D Koharski
Assistant Examiner — Michael Carey
(74) Attorney, Agent, or Firm — David R. Rigney

(57) ABSTRACT

Disclosed methods and devices treat lower back pain from degenerated or injured intervertebral discs. Electrodes connected to a pulse generator deliver electrical impulses to nerves located within the posterior longitudinal ligament and posterior annulus fibrosus of lumbar intervertebral discs. Percutaneous and paddle leads containing the electrodes are disclosed. The percutaneous lead, designed to prevent inappropriate stimulation of the thecal sac, is inserted in the anterior epidural space using a special cannula and lead blank. Paddle leads are configured individually for implantation in each patient. The electrical stimulation may reduce back pain reversibly, with or without the simultaneous use of non-thermal irreversible electroporation. If such stimulation is unsuccessful, nerves in the ligament or annulus fibrosus may then be injured therapeutically without repositioning the lead, using impulses that result in heating, wherein a thermal insulator covers the thecal sac, thereby shielding nerves within the thecal sac from potential heat damage.

43 Claims, 8 Drawing Sheets

(56) References Cited

U.S. PATENT DOCUMENTS

| | | | |
|---|---|---|---|
| 7,331,956 B2 | 2/2008 | Hovda | |
| 7,359,751 B1 | 4/2008 | Erickson | |
| 7,634,307 B2 | 12/2009 | Sweeney | |
| 7,640,064 B2* | 12/2009 | Swoyer | 607/115 |
| 7,738,963 B2 | 6/2010 | Hickman | |
| 7,831,306 B2 | 11/2010 | Finch | |
| 7,894,913 B2 | 2/2011 | Boggs | |
| 7,899,553 B2 | 3/2011 | Barker | |
| 7,930,030 B2 | 4/2011 | Woods | |
| 7,945,331 B2 | 5/2011 | Vilims | |
| 7,949,393 B2 | 5/2011 | Varrichio | |
| 7,979,126 B2 | 7/2011 | Payne | |
| 8,066,702 B2 | 11/2011 | Rittman | |
| 8,086,317 B2 | 12/2011 | Finch | |
| 2005/0261754 A1 | 11/2005 | Woloszko | |
| 2006/0241716 A1* | 10/2006 | Finch et al. | 607/43 |
| 2007/0021803 A1 | 1/2007 | Deem | |
| 2008/0221637 A1* | 9/2008 | Woods et al. | 607/30 |
| 2010/0010567 A1 | 1/2010 | Deem | |
| 2010/0145426 A1* | 6/2010 | Stone | 607/116 |
| 2012/0111730 A1* | 5/2012 | Choi et al. | 205/161 |
| 2013/0338467 A1* | 12/2013 | Grasse et al. | 600/373 |

OTHER PUBLICATIONS

David W.L. Hukins and Judith R. Meakin. Relationship between structure and mechanical function of the tissues of the intervertebral joint. Amer. Zool. 40(2000):42-52.
Panjabi MM. Clinical spinal instability and low back pain. J Electromyogr Kinesiol 13(4,2003):371-379.
Joji Inamasu, Bernard H. Guiot and Donald C. Sachs. Ossification of the Posterior Longitudinal Ligament: An Update on Its Biology, Epidemiology, and Natural History. Neurosurgery 58(6,2006): 1027-1039.
Beatty RA, Sugar O, Fox TA. Protrusion of the posterior longitudinal ligament simulating herniated lumbar intervertebral disc. J Neurol Neurosurg Psychiatry 31(1,1968):61-66.
J.D. Stewart Cauda equina disorders. Chapter 6, pp. 63-74. In: Neurologic Bladder, Bowel and Sexual Dysfunction (Clare J Fowler et al, eds) Amsterdam: Elsevier Science, 2001.
Edgar MA. The nerve supply of the lumbar intervertebral disc. J Bone Joint Surg Br 89(9,2007):1135-1139.
J. Randy Jinkins. The anatomic and physiologic basis of local, referred, and radiating lumbosacral pain syndromes related to disease of the spine. J Neuroradiol 31(2004): 163-180.
Bogduk N, Tynan W, Wilson AS. The nerve supply to the human lumbar intervertebral discs. J Anat 132(1,1981):39-56.
Kojima Y, Maeda T, Arai R, Shichikawa K. Nerve supply to the posterior longitudinal ligament and the intervertebral disc of the rat vertebral column as studied by acetylcholinesterase histochemistry. I. Distribution in the lumbar region. J Anat 169(1990):237-246.
J. H. Mulligan. The innervation of the ligaments attached to the bodies of the vertebrae. J Anat 91(4,1957): 455-465.
Devon I Rubin. Epidemiology and risk factors for spine pain. Neurol Clin 25(2007): 353-371.
Manchikanti L, Singh V, Datta S, Cohen SP, Hirsch JA; American Society of Interventional Pain Physicians. Comprehensive review of epidemiology, scope, and impact of spinal pain. Pain Physician 12(4,2009):E35-E70.
Atlas SJ, Deyo RA. Evaluating and managing acute low back pain in the primary care setting. J Gen Intern Med 16(2,2001):120-131.
Michael Devereaux. Low back pain. Med Clin N America 93(2009):477-501.
Michelle Lin. Musculoskeletal Back Pain. Chapter 51, pp. 591-603. In: Rosen's Emergency Medicine: Concepts and Clinical Practice, 7th edition (Marx JA, Hockberger RS, Walls RM, et al, eds). Philadelphia: Mosby Elsevier, 2009.
Last AR, Hulbert K. Chronic low back pain: evaluation and management. Am Fam Physician 79(12,2009):1067-1074.

McCamey K, Evans P. Low back pain. Prim Care 34(1,2007):71-82.
Chou R, Qaseem A, Snow V, Casey D, Cross JT Jr, Shekelle P, Owens DK; Clinical Efficacy Assessment Subcommittee of the American College of Physicians; American College of Physicians; American Pain Society Low Back Pain Guidelines Panel. Diagnosis and treatment of low back pain: a joint clinical practice guideline from the American College of Physicians and the American Pain Society. Ann Intern Med 147(7,2007): 478-491.
Kallewaard JW, Terheggen MA, Groen GJ, Sluijter ME, Derby R, Kapural L, Mekhail N, van Kleef M. (15.) Discogenic low back pain. Pain Practice 10(6,2010):560-579.
Keith D. Williams and Ashley L. Park. Lower Back Pain and Disorders of Intervertebral Discs. Chapter 39, pp. 2159-2236. In: Campbell's Operative Orthopaedics, 11th edition (S. Terry Canale and James H. Beatty, eds). Philadelphia: Mosby Elsevier, 2007.
Audette JF, Emenike E, Meleger AL. Neuropathic low back pain. Curr Pain Headache Rep 9(3,2005):168-177.
Hurri H, Karppinen J. Discogenic pain. Pain 112(3,2004):225-228.
Freemont AJ, Peacock TE, Goupille P, Hoyland JA, O'Brien J, Jayson MI. Nerve ingrowth into diseased intervertebral disc in chronic back pain. Lancet 350(9072,1997):178-181.
Martin MD, Boxell CM, Malone DG. Pathophysiology of lumbar disc degeneration: a review of the literature. Neurosurg Focus 13(2,2002):Article 1, pp. 1-6.
Peng B, Wu W, Hou S, Li P, Zhang C, Yang Y. The pathogenesis of discogenic low back pain. J Bone Joint Surg Br 87(1,2005): 62-67.
Y. Aoki, K. Takahashi, S. Ohtori & H. Moriya: Neuropathology Of Discogenic Low Back Pain: A Review. The Internet Journal of Spine Surgery 2 (1,2005): 1-9.
Walker MH, Anderson DG. Molecular basis of intervertebral disc degeneration. Spine J 4(6 Suppl, 2004):158S-166S.
Boswell MV, et al. Interventional techniques: evidence-based practice guidelines in the management of chronic spinal pain. Pain Physician 10(1,2007):7-111.
Seaman DR, Cleveland C 3rd. Spinal pain syndromes: nociceptive, neuropathic, and psychologic mechanisms. J Manipulative Physiol Ther 22(7,1999):458-472.
Nakamura SI, Takahashi K, Takahashi Y, Yamagata M, Moriya H. The afferent pathways of discogenic low-back pain. Evaluation of L2 spinal nerve infiltration. J Bone Joint Surg Br 78(4,1996):606-612.
Takebayashi T, Cavanaugh JM, Kallakuri S, Chen C, Yamashita T. Sympathetic afferent units from lumbar intervertebral discs. J Bone Joint Surg Br 88(4,2006):554-557.
Tomecek FJ, Anthony CS, Boxell C, Warren J. Discography interpretation and techniques in the lumbar spine. Neurosurg Focus 13(2,2002):Article 13, pp. 1-8.
Zhang YG, Guo TM, Guo X, Wu SX. Clinical diagnosis for discogenic low back pain. Int J Biol Sci 5(7,2009):647-658.
Manchikanti L, Singh V, Pampati V, Damron KS, Barnhill RC, Beyer C, Cash KA. Evaluation of the relative contributions of various structures in chronic low back pain. Pain Physician 4(4,2001):308-316.
Kinkade S. Evaluation and treatment of acute low back pain. Am Fam Physician 75(8,2007):1181-1188.
Brian S Williams and Paul J Christo. Pharmacological and interventional treatments for neuropathic pain. Chapter 12 pp. 295-375. In: Mechanisms of Pain in Peripheral Neuropathy (M Dobretsov and J-M Zhang, eds). Trivandrum, India: Research Signpost, 2009.
Chou R, Huffman LH; American Pain Society; American College of Physicians. Nonpharmacologic therapies for acute and chronic low back pain: a review of the evidence for an American Pain Society/American College of Physicians clinical practice guideline. Ann Intern Med 147(7,2007): 492-504.
Lavelle WF, Lavelle ED, Smith HS. Interventional techniques for back pain. Clin Geriatr Med 24(2,2008):345-368.
Derby R, Eek B, Chen Y, O'neill C, Ryan D. Intradiscal Electrothermal Annuloplasty (IDET): A Novel Approach for Treating Chronic Discogenic Back Pain. Neuromodulation 3(2,2000):82-88.
Helm S, Hayek SM, Benyamin RM, Manchikanti L. Systematic review of the effectiveness of thermal annular procedures in treating discogenic low back pain. Pain Physician 12(1,2009):207-232.

(56) References Cited

OTHER PUBLICATIONS

Chou R, Baisden J, Carragee EJ, Resnick DK, Shaffer WO, Loeser JD. Surgery for low back pain: a review of the evidence for an American Pain Society Clinical Practice Guideline. Spine 34(10,2009):1094-1109.
Lavelle W, Carl A, Lavelle ED. Invasive and minimally invasive surgical techniques for back pain conditions. Med Clin North Am 91(2,2007):287-298.
Schwender JD, Foley KT, Holly LT, Transfeldt, EE. Minimally Invasive Posterior Surgical Approaches to the Lumbar Spine. Chapter 21, pp. 333-341 In: The Spine, Fifth Edition (Harry N. Herkowitz, Richard A. Balderston, Steven R. Garfin, Frank J. Eismont, eds). Philadelphia: Saunders/Elsevier, 2006.
Griffith SL, Davis RJ, Hutton WC. Repair of the Anulus Fibrosus of the Lumbar Disc. Chapter 12 (pp. 41-48), In: Nucleus Arthroplasty Technology in Spinal Care: vol. II—Biomechanics & Development. Davis R, Cammisa FP, Girardi FP, Hutton WC, Editors. Bloomington, MN: Raymedica Co, 2007.
ten Vaarwerk IA, Staal MJ. Spinal cord stimulation in chronic pain syndromes. Spinal Cord 36(10,1998):671-682.
North RB, Wetzel FT. Spinal cord stimulation for chronic pain of spinal origin: a valuable long-term solution. Spine 27(2,2002):2584-2591.
Stojanovic MP, Abdi S. Spinal cord stimulation. Pain Physician 5(2,2002):156-166.
Barolat G, Sharan A. Spinal Cord Stimulation for Chronic Pain Management. In Pain Management for the Neurosurgeon: Part 2, Seminars in Neurosurgery 15 (2,2004):151-175.
R.B. North. Neural interface devices: spinal cord stimulation technology. Proceedings of the IEEE 96(7,2008):1108-1119.
Abbas Pourzaki and Hossein Mirzaee. New high voltage pulse generators. Recent Patents on Electrical Engineering 2(2009):65-76.
Allen W. Burton, Phillip C. Phan. Spinal Cord Stimulation for Pain Management. Chapter 7, pp. 7-1 to 7-16, In: Neuroengineering (Daniel J. DiLorenzo and Joseph D. Bronzino, eds). Boca Raton: CRC Press, 2008.
Steven Falowski, Amanda Celii, and Ashwini Sharan. Spinal cord stimulation: an update. Neurotherapeutics 5(1,2008):86-99.
Kunnumpurath S, Srinivasagopalan R, Vadivelu N. Spinal cord stimulation: principles of past, present and future practice: a review. J Clin Monit Comput 23(5,2009):333-339.
White PF, Li S, Chiu JW. Electroanalgesia: its role in acute and chronic pain management. Anesth Analg 92(2,2001):505-513.
Stanton-Hicks M, Salamon J. Stimulation of the central and peripheral nervous system for the control of pain. J Clir Neurophysiol 14(1,1997):46-62.
John C. Oakley. Spinal Cord Stimulation in Axial Low Back Pain: Solving the Dilemma. Pain Medicine 7 (Supplements1,2006):S58-S63.
Danner SM, Hofstoetter US, Ladenbauer J, Rattay F, Minassian K. Can the human lumbar posterior columns be stimulated by transcutaneous spinal cord stimulation? A modeling study. Artif Organs 35(3,2011):257-262.
Shealy CN, Mortimer JT, Reswick JB. Electrical inhibition of pain by stimulation of the dorsal columns: preliminary clinical report. Anesth Analg 46(4,1967):489-491.
Sanford J. Larson, Anthony Sances, Joseph F. Cusick, Glenn A. Meyer, Thomas Swiontek. A comparison between anterior and posterior spinal implant systems. Surg. Neurol. 4(1975):180-186.
Reuben Hoppenstein. Electrical stimulation of the ventral and dorsal columns of the spinal cord for relief of chronic intractable pain: preliminary report. Surg. Neurol. 4(1975):187-194.
Mark A. Harrast. Epidural steroid injections for lumbar spinal stenosis. Curr Rev Musculoskelet Med 1:(2008):32-38.
Barolat G, Massaro F, He J, Zeme S, Ketcik B. Mapping of sensory responses to epidural stimulation of the intraspinal neural structures in man. J Neurosurg 78(2,1993):233-239.
Mailis-Gagnon A, Furlan AD, Sandoval JA, Taylor R. Spinal cord stimulation for chronic pain. Cochrane Database Syst Rev. 2004;(3):CD003783, updated 2009, pp. 1-17.

Eldabe S, Kumar K, Buchser E, Taylor RS. An analysis of the components of pain, function, and health-related quality of life in patients with failed back surgery syndrome treated with spinal cord stimulation or conventional medical management. Neuromodulation 13(3,2010):201-209.
Frey ME, Manchikanti L, Benyamin RM, Schultz DM, Smith HS, Cohen SP. Spinal cord stimulation for patients with failed back surgery syndrome: a systematic review. Pain Physician 12(2,2009):379-397.
Vallejo R, Manuel Zevallos L, Lowe J, Benyamin R. Is Spinal Cord Stimulation an Effective Treatment Option for Discogenic Pain? Pain Pract. Jul. 29, 2011. doi: 10.1111/j.1533-2500.2011.00489.x. (Epub ahead of print, pp. 1-8).
Adnan Al-Kaisy, Iris Smet, and Jean-Pierre Van Buyten. Analgesia of axial low back pain with novel spinal neuromodulation. Poster presentation #202 at the 2011 meeting of The American Academy of Pain Medicine, held in National Harbor, MD, Mar. 24-27, 2011.
Kuslich SD, Ulstrom CL, Michael CJ. The tissue origin of low back pain and sciatica: a report of pain response to tissue stimulation during operations on the lumbar spine using local anesthesia. Orthop Clin North Am 22(2,1991):181-187.
Maertens de Noordhout A, Rothwell JC, Thompson PD, Day BL, Marsden CD. Percutaneous electrical stimulation of lumbosacral roots in man. J Neurol Neurosurg Psychiatry 51(2,1988):174-181.
Kothbauer KF, Deletis V. Intraoperative neurophysiology of the conus medullaris and cauda equina. Childs Nerv Syst 26(2,2010):247-253.
Johnson BA, Schellhas KP, Pollei SR. Epidurography and therapeutic epidural injections: technical considerations and experience with 5334 cases. AJNR Am J Neuroradiol 20(4,1999):697-705.
I.S. Lee,S.H. Kim,J.W. Lee,S.H. Hong,J.-Y. Choi,H.S. Kang,J.W. Song, and A.K. Kwon. Comparison of the temporary diagnostic relief of transforaminal epidural steroid injection approaches: conventional versus posterolateral technique. American Journal of Neuroradiology 28(2007): 204-208.
Thomas N. Pajewski, Vincent Arlet and Lawrence H. Phillips. Current approach on spinal cord monitoring: the point of view of the neurologist, the anesthesiologist and the spine surgeon Eur Spine J 16(Suppl 2,2007): 115-129.
Malhotra, Neil R and Shaffrey, Christopher I. Intraoperative electrophysiological monitoring in spine surgery. Spine 35(25,2010):2167-2179.
North RB, Kidd DH, Olin JC, Sieracki JM. Spinal cord stimulation electrode design: prospective, randomized, controlled trial comparing percutaneous and laminectomy electrodes—part I: technical outcomes. Neurosurgery 51(2,2002):381-389.
Pearcy MJ, Tibrewal SB. Lumbar intervertebral disc and ligament deformations measured in vivo. Clin Orthop Relat Res (191,1984):281-286.
MacDonald JD, Fisher KJ. Technique for steering spinal cord stimulator electrode. Neurosurgery 69(1 Suppl Operative, 2011):ons83-86.
A.R. Liboff. Signal shapes in electromagnetic therapies: a primer. pp. 17-37 in: Bioelectromagnetic Medicine (Paul J. Rosch and Marko S. Markov, eds.). New York: Marcel Dekker (2004).
De Vos CC, Hilgerink MP, Buschman HP, Holsheimer J. Electrode contact configuration and energy consumption in spinal cord stimulation. Neurosurgery 65(6 Suppl,2009):210-216.
Holsheimer J. Computer modelling of spinal cord stimulation and its contribution to therapeutic efficacy. Spinal Cord 36(8,1998):531-540.
Gu WY, Justiz MA, Yao H. Electrical conductivity of lumbar annulus fibrosus: effects of porosity and fixed charge density. Spine 27(21,2002):2390-2395.
Lee D, Hershey B, Bradley K, Yearwood T. Predicted effects of pulse width programming in spinal cord stimulation: a mathematical modeling study. Med Biol Eng Comput 49(7,2011):765-774.
Manola L, Holsheimer J, Veltink PH, Bradley K, Peterson D. Theoretical investigation into longitudinal cathodal field steering in spinal cord stimulation. Neuromodulation (2,2007):120-132.
Sekine M, Yamashita T, Takebayashi T, Sakamoto N, Minaki Y, Ishii S. Mechanosensitive afferent units in the lumbar posterior longitudinal ligament. Spine26(14,2001): 1516-1521.

(56) References Cited

OTHER PUBLICATIONS

Coppes MH, Marani E, Thomeer RT, Groen GJ. Innervation of "painful" lumbar discs. Spine 22(20,1997):2342-2349.

von During M, Fricke B, Dahlmann A. Topography and distribution of nerve fibers in the posterior longitudinal ligament of the rat: an immunocytochemical and electron-microscopical study. Cell Tissue Res 281(2,1995):325-338.

McCarthy PW, Petts P, Hamilton A. RT97- and calcitonin gene-related peptide-like immunoreactivity in lumbar intervertebral discs and adjacent tissue from the rat. J Anat 180 (1,1992):15-24.

Ahmed M, Bjurholm A, Kreicbergs A, Schultzberg M. Neuropeptide Y, tyrosine hydroxylase and vasoactive intestinal polypeptide-immunoreactive nerve fibers in the vertebral bodies, discs, dura mater, and spinal ligaments of the rat lumbar spine. Spine 18(2,1993):268-273.

Kallakuri S, Cavanaugh JM, Blagoev DC. An immunohistochemical study of innervation of lumbar spinal dura and longitudinal ligaments. Spine 23(4,1998):403-411.

Gronblad M, Weinstein JN, Santavirta S. Immunohistochemical observations on spinal tissue innervation. A review of hypothetical mechanisms of back pain. Acta Orthop Scand 62(6,1991):614-622.

Kuner R. Central mechanisms of pathological pain. Nat Med 16(11,2010):1258-1266.

Schlereth T, Birklein F. The sympathetic nervous system and pain. Neuromolecular Med 10(3,2008):141-147.

Yongmin Kim, H. Gunter Zieber, and Frank A. Yang. Uniformity of current density under stimulating electrodes. Critical Reviews in Biomedical Engineering 17(1990,6): 585-619.

Habash RW, Bansal R, Krewski D, Alhafid HT. Thermal therapy, part 1: an introduction to thermal therapy. Crit Rev Biomed Eng 34(6,2006):459-489.

Diederich CJ. Thermal ablation and high-temperature thermal therapy: overview of technology and clinical implementation. Int J Hyperthermia 21(8,2005): 745-753.

Haveman J, Van Der Zee J, Wondergem J, Hoogeveen JF, Hulshof MC. Effects of hyperthermia on the peripheral nervous system: a review. Int J Hyperthermia 20(4,2004):371-391.

Lee RC, Zhang D, Hannig J. Biophysical injury mechanisms in electrical shock trauma. Annu Rev Biomed Eng 2(2000):477-509.

Davalos RV, Mir IL, Rubinsky B. Tissue ablation with irreversible electroporation. Ann Biomed Eng 33(2,2005):223-231.

Rubinsky B. Irreversible electroporation in medicine. Technol Cancer Res Treat 6(4,2007):255-260.

Daniels C, Rubinsky B. Electrical field and temperature model of nonthermal irreversible electroporation in heterogeneous tissues. J Biomech Eng 131(7,2009): 071006, pp. 1-12.

* cited by examiner

FIG. 5
FIG. 5A
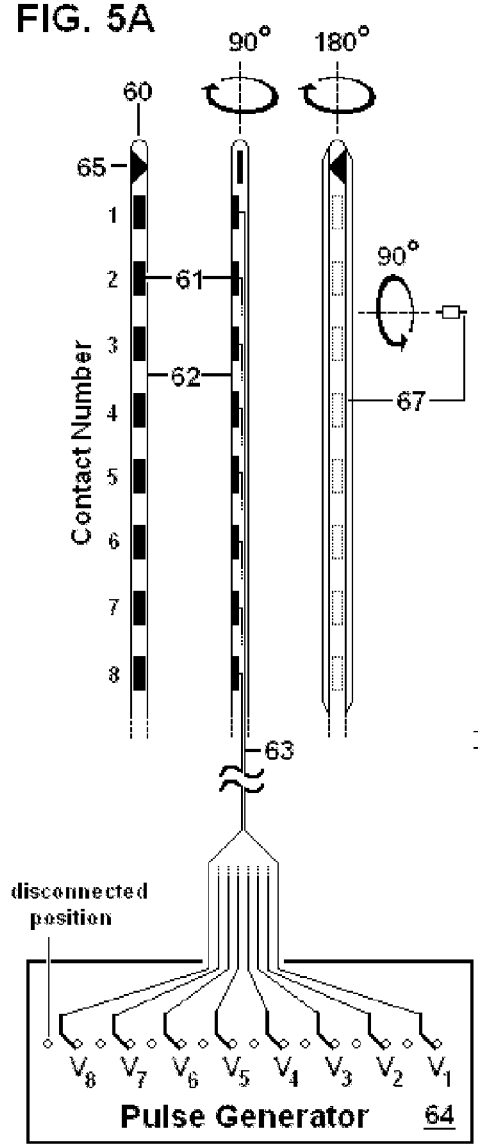
FIG. 5B
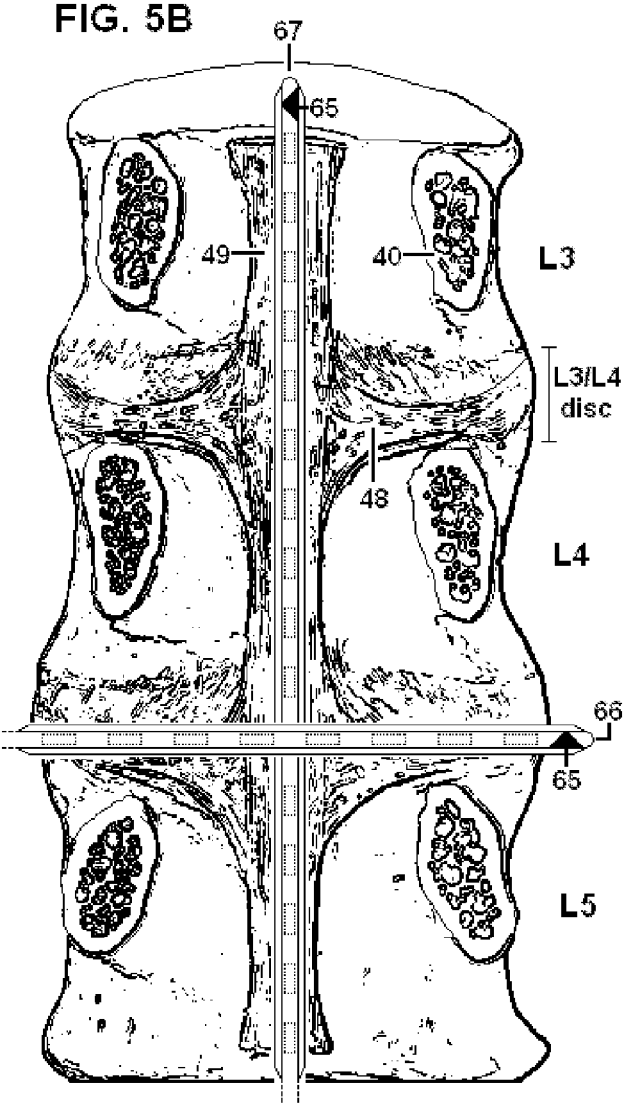

FIG. 6
FIG. 6A
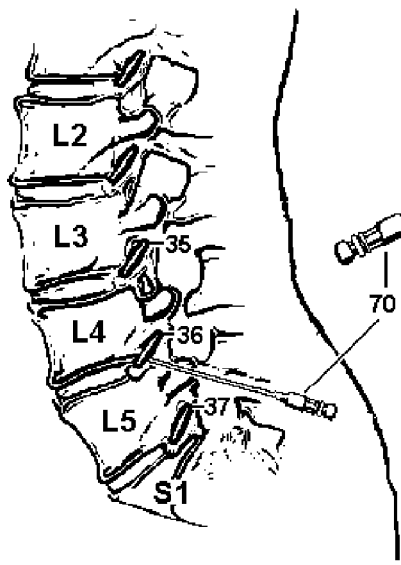
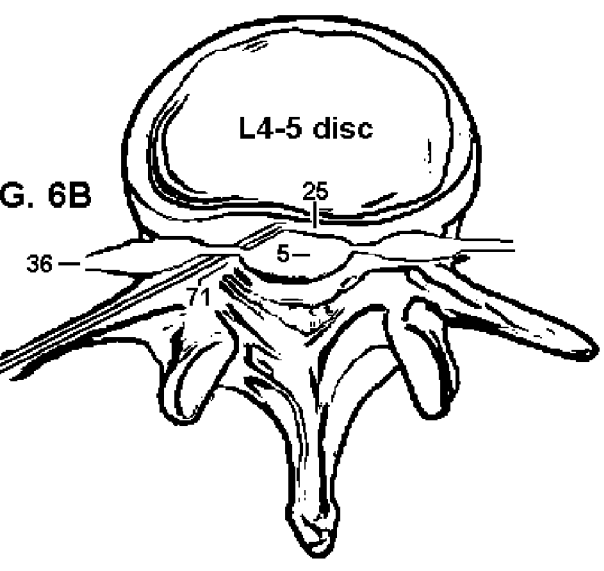
FIG. 6B

FIG. 7
FIG. 7A
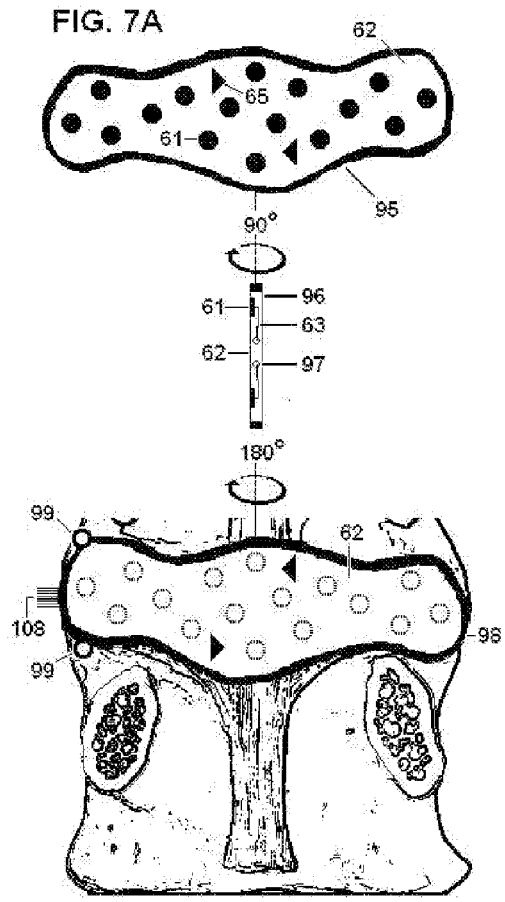
FIG. 7B
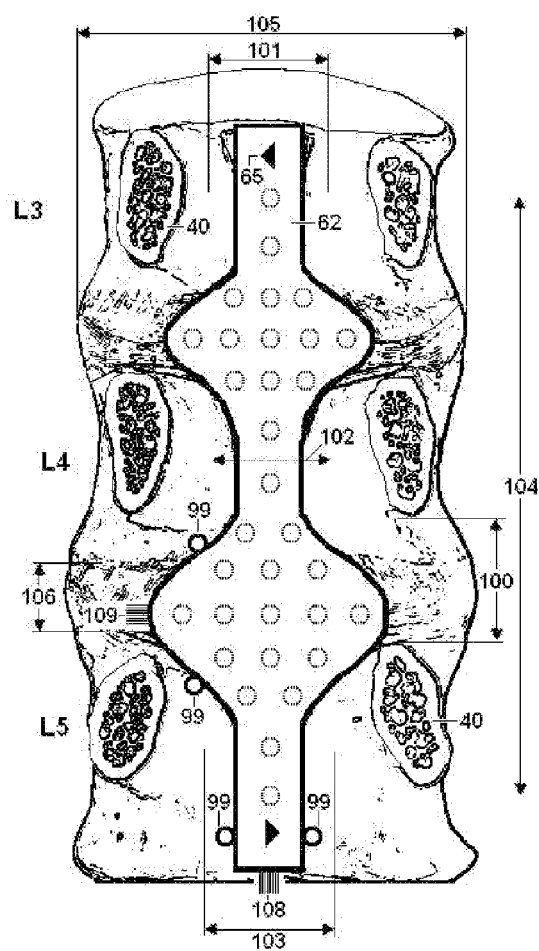

SYSTEM AND METHOD FOR ELECTRICAL STIMULATION OF THE LUMBAR VERTEBRAL COLUMN

CROSS REFERENCE TO RELATED APPLICATIONS

This is a division of pending U.S. application Ser. No. 13/402,093 having publication No. US 2012/0215218, which was filed 22 Feb. 2012. That application, as well as this division of that application, claims the benefit of provisional patent application No. 61/463,800, entitled System and Method for Electrical Stimulation of the Lumbar Vertebral Column, to J. D. LIPANI, with a filing date of Feb. 23, 2011, the complete disclosure of which is incorporated herein by reference for all purposes.

BACKGROUND OF THE INVENTION

The field of the present invention relates to the delivery of energy impulses to bodily tissues for therapeutic purposes, particularly the use of implanted electrical stimulators. The disclosed methods and devices may be used to treat discogenic lower back pain, by selectively stimulating nerves that innervate a posterior longitudinal ligament and/or the adjacent outer posterior annulus fibrosus of a lumbar disc.

More specifically, the present invention is directed to methods and devices for the treatment of chronic lower back pain that may result from a degenerated or injured intervertebral disc, or paraspinal-mediated low back pain.

Electrodes, along with a pulse generator that is connected to the electrodes, are used to deliver electrical impulses to nociceptive and/or other nerves located within the posterior longitudinal ligament of the lumbar spine and the posterior annulus fibrosus of the intervertebral disc(s) that lies adjacent to the posterior longitudinal ligament. According to the invention, the electrical stimulation in this region may reduce back pain in a patient reversibly, adjustably, and with almost complete coverage of the pain-generating region, for example, by interfering with or modulating afferent pain signals to the brain that originate in those nerves. Alternatively, if the reversible electrical stimulation is unsuccessful in alleviating the back pain, electrical stimulation parameters may be selected so as to irreversibly damage the ability of the nerves to send pain signals to the brain, using non-thermal irreversible electroporation. In a different embodiment, the device may be used to relieve pain in the patient by irreversibly damaging nerves in the posterior longitudinal ligament and/or posterior annulus fibrosus by joule heating and/or by dielectric heating of proteins, wherein a thermal insulator covers substantially all of the cauda equina or thecal sac, thereby shielding the cauda equina or thecal sac from the heat that could cause damage.

The disclosed methods involve the implantation of electrically stimulating electrodes within the anterior epidural space, adjacent to the posterior longitudinal ligament (PLL) of the lumbar spine. Such implantation is disclosed in detail below, but for purposes of providing background information, the relevant anatomy of the spine and vertebrae will first be summarized and illustrated in FIGS. 1 to 4.

Proceeding from the neck to the tailbone, there are 7 cervical (neck) vertebrae (C1-C7), 12 thoracic vertebrae (T1-T12), and 5 lumbar vertebrae (L1-L5). This is followed by the 5 sacral and coccyx (tailbone) vertebrae, which are inserted like a wedge between the two hip bones. The present invention is concerned primarily with the lumbar vertebrae L3 to L5, although it is understood that the invention may be adapted for use in other vertebrae as well, for example, the lumbar vertebrae L1 to L3, or the sacral vertebrae.

The vertebral column comprises bony vertebral bodies that are separated by cartilaginous intervertebral discs. A primary function of the vertebral column is to provide mechanical support for the body. The intervertebral discs provide a cushion between the vertebral bodies, absorbing some of the axial load and also facilitating motion within the vertebral column. Each disc contains a soft gel-like center (the nucleus pulposus), which is constrained radially by an elastic outer band, the annulus fibrosus. Each vertebral body articulates with its neighboring vertebral body above and below, which allows for some degree of flexion, extension, and rotation [HUMZAH M D, Soames R W. Human intervertebral disc: structure and function. Anat Rec 220(4, 1988):337-56].

Ligaments connect two or more bones and help stabilize joints. The present invention is concerned particularly with the posterior longitudinal ligament (PLL), which runs axially along the interior portion of the vertebral bodies and of the annulus fibrosus of the discs that lie between the vertebral bodies. The PLL protects the discs and imparts stability during flexion of the body [David W. L Hukins and Judith R. Meakin. Relationship between structure and mechanical function of the tissues of the intervertebral joint. Amer. Zool. 40 (2000):42-52]. Furthermore, nerves that innervate the PLL may participate in reflex loops that cause back muscles to stabilize the spine.

Thus, neural receptors in the posterior longitudinal ligament, simultaneously with the output of the receptors from other ligaments such as the supraspinal ligament, as well as receptors in the discs, are thought to add their neural outputs to spinal interneurons, so as to reflexly activate the multifidus and longissimus muscles of the back in order to stabilize the spine in response to loads and movements [PANJABI MM. Clinical spinal instability and low back pain. J Electromyogr Kinesiol 13(4,2003):371-9].

The posterior longitudinal ligament may be injured (sprained, as a stretch and/or tear) as the result of sudden violent contraction, sudden torsion, lifting a heavy object, or other acute mechanical events.

Because the PLL lies adjacent to the posterior annulus fibrosus of the intervertebral disc, inflammation of the disc that results from degeneration or herniation of the disc may secondarily contribute to dysfunction of the PLL, e.g., via inflammatory mediators. The most thoroughly investigated disease of the PLL itself is its ossification, which is more common in the cervical (70%), as compared to either thoracic (15%) or lumbar (15%) regions [Joji INAMASU, Bernard H. Guiot and Donald C. Sachs. Ossification of the Posterior Longitudinal Ligament: An Update on Its Biology, Epidemiology, and Natural History. Neurosurgery 58(6, 2006): 1027-1039]. The PLL may also fold and compress a nerve root [BEATTY R A, Sugar O, Fox T A. Protrusion of the posterior longitudinal ligament simulating herniated lumbar intervertebral disc. J Neurol Neurosurg Psychiatry 31(1, 1968):61-6].

Each vertebra is composed of the above-mentioned vertebral body (anteriorly) and an arch (posteriorly). Processes protrude from each arch and serve as points of attachment for muscles of the back. A spinous process protrudes backwards on each arch, and transverse processes extend from the lateral edges of each arch. The parts of the arch between the spinous and transverse processes are known as laminae, and the parts of the arch between the transverse processes and the body are known as pedicles. At the point where the laminae and pedicles meet, each vertebra contains two superior articular facets and two inferior articular facets. The pedicle of each vertebra is notched at its superior and inferior edges. Together the notches from two contiguous vertebra form an opening, the intervertebral neural foramen, through which spinal nerves pass.

A vertebral arch also contains an opening (the vertebral foramen) which forms a canal through which the spinal cord passes, protecting the spinal cord and nerve roots that exit from it. Because the spinal cord stops growing in infancy while the bones of the spine continue to grow, the spinal cord in adults ends at about the level of the vertebra L1/L2. Below that vertebral level, a bundle-like structure of nerve fibers, known as the cauda equina, occupy the vertebral foramen, which emanates from the terminus of the spinal cord (the conus medullaris). Thus, the lumbar vertebral foramen surrounds the spinal cord/conus medullaris above vertebrae L1/L2 and the cauda equina nerve roots below vertebrae L1/L2. [J. D. STEWART Cauda equina disorders. Chapter 6, pp 63-74. In: Neurologic Bladder, Bowel and Sexual Dysfunction (Clare J Fowler et al, eds) Amsterdam: Elsevier Science, 2001].

The above-mentioned structures are illustrated in FIGS. 1 to 4. Features shown in those figures that are particularly relevant to the present invention include the locations of the posterior longitudinal ligament (PLL) and the annulus fibrosus of the intervertebral disc(s) that lies adjacent to the PLL. For future reference, the location of electrodes of the present invention, which are implanted adjacent to the PLL, is also shown in FIGS. 1-4 (item 6 in FIG. 1, item 6 in FIG. 2, item 6 in FIG. 3, and within regions 50 and/or 51 in FIG. 4).

FIG. 1 shows the spine in a cross section perpendicular to its long axis, cut through one of the lumbar discs. The interconnections between the nerves that are shown in FIG. 1 are relevant to the mechanism by which the disclosed electrical stimulation of nerves innervating the PLL and annulus fibrosus may reduce back pain [EDGAR M A. The nerve supply of the lumbar intervertebral disc. J Bone Joint Surg Br 89(9, 2007):1135-9]. Structures labeled in FIG. 1 are as follows: nucleus pulposus 1; annulus fibrosus 2; anterior longitudinal ligament 3; posterior longitudinal ligament 4; thecal sac 5; electrodes of the present invention situated in the anterior epidural space 6; filum terminale 7; intrathecal nerve root of the cauda equina 8; ventral nerve root 9; dorsal nerve root 10; dorsal root ganglion 11; dorsal ramus of the spinal nerve 12; medial branch of the dorsal ramus 13; sinuvertebral nerve (meningeal branch of the spinal nerve) 14; connecting sympathetic branch from gray ramus to sinuvertebral nerve 15; neural radicals from sinuvertebral nerve to disc 16; white ramus communicans 17; gray ramus communicans 18; sympathetic neural radicals to disc surface 19; paraspinal sympathetic ganglion 20; paraspinal sympathetic chain 21; anterior branch from sympathetic ganglion to disc surface 22; branches from sympathetic ganglion to disc surface 23; and posterior epidural space 24. FIG. 1 is adapted from: J. Randy JINKINS. The anatomic and physiologic basis of local, referred, and radiating lumbosacral pain syndromes related to disease of the spine. J Neuroradiol 31 (2004): 163-180.

FIG. 2 shows a section of the spine viewed from the side (left-to-right). The section is angled slightly away from the midline of the back, so as to demonstrate many of the ligaments of the spine. Vertebral bodies are labeled T12 through S1 as shown. Structures otherwise labeled in FIG. 2 are as follows: anterior longitudinal ligament 3; posterior longitudinal ligament 4; spinal cord 26; cauda equina 27; membrane of dura mater that surrounds the spinal cord and the cauda equina (thecal sac, dural tube) containing cerebral spinal fluid 5; electrodes of the present invention situated in anterior epidural space 6; posterior epidural space 24; anterior epidural space 25; intervertebral disc 29; ligamentum flavum 30; interspinous ligament 31; supraspinous ligament 32; sacrococcygeal ligament 33; and sacral hiatus 34.

FIG. 3 shows a posterior-to-anterior view of the lumbar spine, viewed obliquely on the left side of the patient. Vertebral bodies are labeled L3 through L5 as shown. The structures that are otherwise labeled in FIG. 3 are as follows: posterior longitudinal ligament 4; electrodes of the present invention situated in anterior epidural space 6; membrane of dura mater that surrounds the cauda equina (thecal sac, dural tube), containing cerebral spinal fluid 5; cauda equina nerve roots 27; intervertrbal disc 29; ligamentum flavum 30; L3 nerve root 35; L4 nerve root 36; L5 nerve root 37; pedicle (cut) 40; lamina (cut) 41; spinous process 42; transverse process 43; superior articular process 44; and facet joint 45.

The present invention electrically stimulates nerves in the PLL, the connective tissue between the PLL and annulus fibrosus and/or periosteum, and in the superficial layer of the dorsal aspect of the annulus fibrosus that lies under the PLL [BOGDUK N, Tynan W, Wilson A S. The nerve supply to the human lumbar intervertebral discs. J Anat 132(1, 1981):39-56; EDGAR M A. The nerve supply of the lumbar intervertebral disc. J Bone Joint Surg Br 89(9, 2007):1135-9; KOJIMA Y, Maeda T, Arai R, Shichikawa K. Nerve supply to the posterior longitudinal ligament and the intervertebral disc of the rat vertebral column as studied by acetylcholinesterase histochemistry. I. Distribution in the lumbar region. J Anat 169 (1990):237-46; J. H. MULLIGAN. The innervation of the ligaments attached to the bodies of the vertebrae. J Anat 91(4, 1957): 455-465]. FIG. 4 shows a posterior-to-anterior view of the innervation of the posterior longitudinal ligament (PLL) and of the annulus fibrosus of the intervertebral disc that lies adjacent to the PLL. In this view, many of the structures shown in FIG. 3 are removed. Structures labeled in FIG. 4 are as follows: posterior longitudinal ligament 4; intervertebral fibers of the PLL 48; vertebral (longitudinal) fibers of the PLL 49; sinuvertebral nerve 14; nerve root 38; pedicle (cut) 40; horizontal region that may be stimulated by the disclosed devices 50; and vertical (longitudinal) region that may be stimulated by the disclosed devices 51.

Low back pain is extremely prevalent and is the second most common reason for patients to seek medical attention. Pain may be elicited during times of overexertion that results in sprain, strain, or spasm in one or more of the muscles or ligaments in the back. If the spine becomes overly strained or compressed, a disc may rupture or bulge outward. Prolonged stresses or degenerative changes facilitated by obesity, smoking, arthritis, poor posture, or unhealthy activity-related habits may result in injury to the intervertebral disc, resulting in chronic discogenic-mediated low back pain [Devon I RUBIN. Epidemiology and risk factors for spine pain. Neurol Clin 25 (2007): 353-371; MANCHIKANTI L, Singh V, Datta S, Cohen S P, Hirsch J A; American Society of Interventional Pain Physicians. Comprehensive review of epidemiology, scope, and impact of spinal pain. Pain Physician 12(4, 2009): E35-70].

Acute back pain tends to come on suddenly, but also tends to improve in a short period of time with short-term conservative treatment, such as medication, exercise, physical therapy or rest [ATLAS S J, Deyo R A. Evaluating and managing acute low back pain in the primary care setting. J Gen Intern Med 16(2, 2004120-31]. Chronic back pain is commonly described as deep, aching, dull or burning pain in one area of the back, which may also travel down the leg(s). It tends to last a month or more or may be a persistent unrelenting problem. Sciatica is pain that begins in the hip and/or buttocks and travels down the back of the leg. There are many causes of chronic back pain, including some that are from intra-abdominal disorders that can cause pain to be referred to the back. Other examples of causes of back pain are as follows: A radiculopathy can be due to a pinched nerve resulting from a herniated disc; sciatica can be due to pinched nerves in vertebrae L4-53; central spinal stenosis is due to narrowing of the spinal canal; foraminal stenosis is due to bone spurs that protrude into the neural foramen and put pressure on a nerve root; and low back pain can also be due to gradual loss of normal spinal structure associated with spondylosis, spinal osteoarthritis, and/or degenerative disc disease [Michael DEVEREAUX. Low back pain. Med Clin N America 93 (2009):477-501; Michelle LIN. Musculoskeletal Back Pain. Chapter 51, pp 591-603. In: Rosen's Emergency Medicine: Concepts and Clinical Practice, 7th edition (Marx J A, Hockberger R S, Walls R M, et al, eds). Philadelphia: Mosby Elsevier, 2009; LAST A R, Hulbert K. Chronic low back pain: evaluation and management. Am Fam Physician 79(12, 2009):1067-74; McCAMEY K, Evans P. Low back pain. Prim Care 34(1, 2007):71-82]. CHOU et al provide a flowchart to assist in the diagnosis and subsequent treatment of low back pain [CHOU R, Qaseem A, Snow V, Casey D, Cross J T Jr, Shekelle P, Owens D K; Clinical Efficacy Assessment Subcommittee of the American College of Physicians; American College of Physicians; American Pain Society Low Back Pain Guidelines Panel. Diagnosis and treatment of low back pain: a joint clinical practice guideline from the American College of Physicians and the American Pain Society. Ann Intern Med 147(7, 2007): 478-91].

The present invention is concerned primarily with back pain that is due to degenerative disc disease, wherein degenerative changes following loss of hydration of the nucleus pulposus lead to circumferential or radial tears within the annulus fibrosus. Annular tears within the outer annulus stimulate the ingrowth of blood vessels and accompanying nociceptors into the outer annulus, for example, from the overlying posterior longitudinal ligament. Nerve endings are recruited to the area of injury and sensitized by inflammatory cytokines and other chemofactors. Pain transmission is then sustained by chronic inflammation and exacerbated by constant axial loading [KALLEWAARD J W, Terheggen M A, Groen G J, Sluijter M E, Derby R, Kapural L, Mekhail N, van Kleef M. (15.) Discogenic low back pain. Pain Practice 10(6, 2010):560-79; Keith D. WILLIAMS and Ashley L. Park. Lower Back Pain and Disorders of Intervertebral Discs. Chapter 39, pp. 2159-2236. In: Campbell's Operative Orthopaedics, 11th edition (S. Terry Canale and James H. Beatty, eds). Philadelphia: Mosby Elsevier, 2007; AUDETTE J F, Emenike E, Meleger A L. Neuropathic low back pain. Curr Pain Headache Rep 9(3, 2005):168-77; HURRI H, Karppinen J. Discogenic pain. Pain 112(3, 2004):225-8; FREEMONT A J, Peacock T E, Goupille P, Hoyland J A, O'Brien J, Jayson M I. Nerve ingrowth into diseased intervertebral disc in chronic back pain. Lancet 350(9072, 1997):178-81].

Although the pathophysiology of degenerative disc disease is incompletely understood, it is thought that sensitization of these nociceptors by various inflammatory repair mechanisms may lead to chronic discogenic pain [MARTIN M D, Boxell C M, Malone D G. Pathophysiology of lumbar disc degeneration: a review of the literature. Neurosurg Focus 13(2, 2002):Article 1, pp. 1-6; PENG B, Wu W, Hou S, Li P, Zhang C, Yang Y. The pathogenesis of discogenic low back pain. J Bone Joint Surg Br 87(1, 2005): 62-7; Y. AOKI, K. Takahashi, S. Ohtori & H. Moriya: Neuropathology Of Discogenic Low Back Pain: A Review. The Internet Journal of Spine Surgery 2 (1, 2005): 1-9; WALKER M H, Anderson D G. Molecular basis of intervertebral disc degeneration. Spine J 4(6 Suppl, 2004):1585-166S; BOSWELL M V, et al. Interventional techniques: evidence-based practice guidelines in the management of chronic spinal pain. Pain Physician 10(1, 2007):7-111; J. Randy JINKINS. The anatomic and physiologic basis of local, referred, and radiating lumbosacral pain syndromes related to disease of the spine. J Neuroradiol 31 (2004): 163-180; SEAMAN D R, Cleveland C 3rd. Spinal pain syndromes: nociceptive, neuropathic, and psychologic mechanisms. J Manipulative Physiol Ther 22(7, 1999):458-72; NAKAMURA S I, Takahashi K, Takahashi Y, Yamagata M, Moriya H. The afferent pathways of discogenic low-back pain. Evaluation of L2 spinal nerve infiltration. J Bone Joint Surg Br 78(4, 1996):606-12; TAKEBAYASHI T, Cavanaugh J M, Kallakuri S, Chen C, Yamashita T. Sympathetic afferent units from lumbar intervertebral discs. J Bone Joint Surg Br 88(4, 2006):554-7].

The current standard for diagnosing discogenic pain is pressure-controlled provocative discography [TOMECEK F J, Anthony C S, Boxell C, Warren J. Discography interpretation and techniques in the lumbar spine. Neurosurg Focus 13(2, 2002):Article 13, pp 1-8; ZHANG Y G, Guo T M, Guo X, Wu S X. Clinical diagnosis for discogenic low back pain. Int J Biol Sci 5(7, 2009):647-58]. Diagnostic nerve blockade may also be used to characterize the nerve source of the low back pain [MANCHIKANTI L, Singh V, Pampati V, Damron K S, Barnhill R C, Beyer C, Cash K A. Evaluation of the relative contributions of various structures in chronic low back pain. Pain Physician 4(4, 2001)308-16].

Several therapies have been used to target the nociceptive nerve fibers within the affected discs in patients with discogenic back pain. Non-surgical techniques involve pain medication and physical therapy with behavioral modification [KINKADE S. Evaluation and treatment of acute low back pain. Am Fam Physician 75(8, 2007):1181-8; Brian S WILLIAMS and Paul J. Christo. Pharmacological and interventional treatments for neuropathic pain. Chapter 12, pp 295-375. In: Mechanisms of Pain in Peripheral Neuropathy (M Dobretsov and J-M Zhang, eds). Trivandrum, India: Research Signpost, 2009; CHOU R, Huffman L H; American Pain Society; American College of Physicians. Nonpharmacologic therapies for acute and chronic low back pain: a review of the evidence for an American Pain Society/American College of Physicians clinical practice guideline. Ann Intern Med 147(7, 2007): 492-504].

Other destructive minimally invasive and surgical techniques have been used when conservative measures fail [BOSWELL M V, et al. Interventional techniques: evidence-based practice guidelines in the management of chronic spinal pain. Pain Physician 10(1, 2007):7-111; LAVELLE W F, Lavelle E D, Smith H S. Interventional techniques for back pain. Clin Geriatr Med 24(2, 2008):345-68]. Minimally invasive techniques include Intradiscal electrothermal therapy (IDET), which involves the application of heat via a needle that is inserted transcutaneously into the disc [DERBY R, Eek B, Chen Y, O'neill C, Ryan D. Intradiscal Electrothermal Annuloplasty (IDET): A Novel Approach for Treating Chronic Discogenic Back Pain. Neuromodulation 3(2, 2000): 82-8]. Alternatively, radiofrequency annuloplasty is a technique used to target the affected area using a needle to deliver radiofrequency energy for destructive purposes [HELM S, Hayek S M, Benyamin R M, Manchikanti L. Systematic review of the effectiveness of thermal annular procedures in treating discogenic low back pain. Pain Physician 12(1, 2009):207-32]. Rather than using heat to destroy nerves in the affected area, it has been proposed that they may be destroyed using ionizing radiation [U.S. Pat. No. 7,634,307, entitled Method and apparatus for treatment of discogenic pain, to SWEENEY].

Surgical techniques are also used to remove a large portion of the disc followed by a fusion procedure between the two adjoining vertebral bodies [CHOU R, Baisden J, Carragee E J, Resnick D K, Shaffer W O, Loeser J D. Surgery for low back pain: a review of the evidence for an American Pain Society Clinical Practice Guideline. Spine 34(10, 2009):1094-109; LAVELLE W, Carl A, Lavelle ED. Invasive and minimally invasive surgical techniques for back pain conditions. Med Clin North Am 91(2, 2007):287-98; SCHWENDER J D, Foley K T, Holly L T, Transfeldt, E E. Minimally Invasive Posterior Surgical Approaches to the Lumbar Spine. Chapter 21, pp. 333-341 In: The Spine, Fifth Edition (Harry N. Herkowitz, Richard A. Balderston, Steven R. Garfin, Frank J. Eismont, eds). Philadelphia: Saunders/Elsevier, 2006; GRIFFITH S L, Davis R J, Hutton W C. Repair of the Anulus Fibrosus of the Lumbar Disc. Chapter 12 (pp 41-48), In: Nucleus Arthroplasty Technology in Spinal Care: Volume II-Biomechanics & Development. Davis R, Cammisa F P, Girardi F P, Hutton W C, Editors. Bloomington, Minn.: Raymedica Co, 2007].

As described in the above-cited publications, all of these techniques have varying degrees of success, and pain relief is generally temporary. A problem with IDET and similar minimally invasive techniques is that destruction of nociceptors within the posterior annulus is variable and incomplete. In addition, the offending region involving the PLL is not addressed.

Several patents or patent applications disclose methods similar to radiofrequency annuloplasty, wherein an array of electrodes (a lead) is introduced into the disc (but not into the epidural space adjacent to the disc) to thermally ablate disc tissue. In U.S. Pat. No. 8,066,702, entitled Combination electrical stimulating and infusion medical device and method, to RITTMAN, III, et al., radiofrequency energy is transmitted to tissue surrounding the lead, thereby ablating the tissue. U.S. Pat. No. 6,772,012 and U.S. Pat. No. 7,270,659, entitled Methods for electrosurgical treatment of spinal tissue, to RICART et al., also describe controlled heating to ablate various tissues in or around the vertebral column using a radiofrequency voltage, including possibly a posterior longitudinal ligament. A thermal ablation method that may also be directed to the posterior longitudinal ligament, involving electrosurgically coagulating nerve tissue within the posterior of the annulus fibrosus by applying heat, is disclosed in U.S. Pat. No. 7,331,956, entitled Methods and apparatus for treating back pain, to HOVDA et al. Similarly, abandoned application U.S. Ser. No. 11/105,274, corresponding to publication No. US20050261754, entitled Methods and apparatus for treating back pain, to WOLOSZKO et al., describes denervation of an intervertebral disc or a region of the posterior longitudinal ligament by the controlled application of heat to a target tissue. All of the methods disclosed in those patents affect the offending region irreversibly, through the application of joule heating. In contrast, in the preferred embodiments of the present invention, electrodes are introduced to affect the offending region reversibly, not irreversibly. Alternatively, in another embodiment of the present invention, the offending region may be affected irreversibly, but in contrast to the above-mentioned patents, the irreversible damage is due to electroporation, not heating. In yet another embodiment of the present invention, irreversible damage through heating is also possible. However, in contrast to the patents cited above, an implanted lead that may be initially used for reversible stimulation and non-thermal electroporation may be used for the heating as well, without repositioning, wherein the thecal sac is shielded from the heat that could cause damage.

Lower back pain has been treated reversibly by stimulation of the spinal cord, using electrical stimulation devices that are used generically to modulate neuronal function [ten VAARWERK I A, Staal M J. Spinal cord stimulation in chronic pain syndromes. Spinal Cord 36(10, 1998):671-82; NORTH R B, Wetzel F T. Spinal cord stimulation for chronic pain of spinal origin: a valuable long-term solution. Spine 27(2, 2002): 2584-91; STOJANOVIC M P, Abdi S. Spinal cord stimulation. Pain Physician 5(2, 2002):156-66; BAROLAT G, Sharan A. Spinal Cord Stimulation for Chronic Pain Management. In Pain Management for the Neurosurgeon: Part 2, Seminars in Neurosurgery 15 (2, 2004):151-175; R. B. NORTH. Neural interface devices: spinal cord stimulation technology. Proceedings of the IEEE 96(7, 2008): 1108-1119; Allen W. BURTON, Phillip C. Phan. Spinal Cord Stimulation for Pain Management. Chapter 7, pp. 7-1 to 7-16, In: Neuroengineering (Daniel J. DiLorenzo and Joseph D. Bronzino, eds). Boca Raton: CRC Press, 2008; Steven FALOWSKI, Amanda Celii, and Ashwini Sharan. Spinal cord stimulation: an update. Neurotherapeutics 5(1, 2008): 86-99; KUNNUMPURATH S, Srinivasagopalan R, Vadivelu N. Spinal cord stimulation: principles of past, present and future practice: a review. J Clin Monit Comput 23(5, 2009): 333-9]. Other examples of electrical stimulation are deep brain stimulation for treatment of Parkinson's disease or other movement disorders, complex regional pain syndrome (previously referred to as reflex sympathetic dystrophy), post herpetic neuralgia and others. In addition to centrally mediated nerve stimulation, peripheral nerve stimulation has also been used to successfully treat neuropathic pain syndromes such as occipital, trigeminal, and post herpetic neuralgias [WHITE P F, Li S, Chiu J W. Electroanalgesia: its role in acute and chronic pain management. Anesth Analg 92(2, 2001):505-13; STANTON-HICKS M, Salamon J. Stimulation of the central and peripheral nervous system for the control of pain. J Clin Neurophysiol 14(1, 1997):46-62].

Although spinal cord electrical stimulation is an established method for treating axial lower back pain, it produces improvement in back pain in only approximately 50% of patients [John C. OAKLEY. Spinal Cord Stimulation in Axial Low Back Pain: Solving the Dilemma. Pain Medicine 7 (Supplement s1, 2006):558-563]. The devices used for spinal cord stimulation comprise: (1) electrodes that are implanted in the spine, and (2) a power source that delivers electrical pulses to the electrodes. The present invention also discloses electrodes that are implanted in the spine and a power source that powers the electrical pulses that are delivered to the electrodes.

Commercially available general-purpose electrodes and pulse generators that are used for spinal cord stimulation and peripheral nerve stimulation could in principle also be used to electrically stimulate the lumbar posterior longitudinal ligament and adjoining outer posterior annulus fibrosus of the intervertebral discs. However, as disclosed below, such general-purpose stimulators are not well-suited for the objectives of the present invention. Furthermore, devices according to the present invention are not spinal cord stimulators for treating back pain. In fact, electrodes in the present invention are placed in the canal defined by the vertebral foramen in the lumbar region and in most cases, below the spinal cord, where the cauda equina rather than the spinal cord occupies that opening. Heretofore, when the lumbar columns have been stimulated with spinal cord stimulator devices, it has been for purposes of spasticity control or the generation of muscle activity in spinal cord injury patients, not for purposes of treating back pain [DANNER S M, Hofstoetter U S, Ladenbauer J, Rattay F, Minassian K. Can the human lumbar posterior columns be stimulated by transcutaneous spinal cord stimulation? A modeling study. Artif Organs 35(3, 2014257-62]. In order to explain differences between the present invention and spinal cord stimulators, the development and use of spinal cord stimulators will first be summarized.

Spinal cord electrical stimulation for the treatment of pain was first performed in 1967 by SHEALY and colleagues [SHEALY C N, Mortimer J T, Reswick J B. Electrical inhibition of pain by stimulation of the dorsal columns: preliminary clinical report. Anesth Analg 46(4, 1967):489-91]. In the decade that followed, many variations in technique were tried. Electrodes were implanted at different locations relative to the spinal cord: in endodural, subdural, subarachnoid, and epidural positions. To do so, a significant amount of spinal bone was often removed, in order to allow placement of the electrodes (a surgical laminectomy, or complete removal of vertebral lamina). In other cases, a small window of bone was drilled over the area, using less invasive techniques (laminotomy, or partial removal of vertebral lamina). Finally, minimally invasive techniques were developed to implant a catheter-like electrode lead percutaneously.

Rather than implanting the electrodes one-by-one, leads (also known as electrode arrays) were developed wherein multiple electrodes were mounted on, in, or about an insulating substrate, and the lead was then implanted. Such leads may have the shape of a plate and are said to contain paddle electrodes, plate electrodes, ribbon electrodes, surgical electrodes or laminotomy electrodes. For percutaneous implantation, the leads may also have the shape of a wire or catheter, which are said to contain percutaneous or wire electrodes.

In almost all cases, the electrodes were implanted on the posterior side of the spinal cord, i.e., the side most accessible from the back. However, in 1975 LARSON et al. and HOPPERSTEIN implanted electrodes on the anterior side of the spinal column, in an attempt to improve the low success rate of spinal cord stimulation in reducing pain [Sanford J. LARSON, Anthony Sances, Joseph F. Cusick, Glenn A. Meyer, Thomas Swiontek. A comparison between anterior and posterior spinal implant systems. Surg. Neurol. 4 (1975):180-186; Reuben HOPPENSTEIN. Electrical stimulation of the ventral and dorsal columns of the spinal cord for relief of chronic intractable pain: preliminary report. Surg. Neurol. 4 (1975):187-194]. In contrast to the present invention, though, they did not implant the anterior electrodes within the anterior epidural space, they did not attempt to implant electrodes in the lumbar spine, and they were not concerned with the treatment of back pain. Furthermore, the anteriorly-placed electrodes were configured to stimulate the spinal cord, which is different than the configuration that would stimulate only nerves in the posterior longitudinal ligament and the underlying annulus fibrosus as in the present invention.

The anterior location of the electrode in the epidural space is particularly relevant to the present invention. The epidural space is the space within the spinal canal lying outside the dura mater (dural or thecal sac), which contains lymphatics, spinal nerve roots, loose fatty tissue, small arteries, and blood vessels. The epidural space surrounds the dural sac and is bounded by the posterior longitudinal ligament anteriorly, the ligamenta flava and the periosteum of the laminae posteriorly, and the pedicles of the spinal column and the intervertebral neural foramina containing their neural elements laterally. The space communicates freely with the paravertebral space through the intervertebral neural foramina. For spinal cord stimulation, the electrodes are now invariably implanted in the posterior epidural space.

However, a percutaneous lead may be accidentally introduced into the anterior epidural space, which is considered to be an error, and the lead is withdrawn. Thus, FALOWSKI et al. write that "Frequently, the electrode curves around the dural sac and ends in the ventral epidural space. A gentle lateral curve of the electrode shortly after its entry into the epidural space should arouse the suspicion that it is directing ventrally around the dural sac. Absolute confirmation of the ventral location arises from the stimulation generating violent motor contractions or observation [by fluoroscopy] in the lateral plane which would readily disclose the anterior position of the electrode tip." [Steven FALOWSKI, Amanda Celii, and Ashwini Sharan. Spinal cord stimulation: an update. Neurotherapeutics 5(1, 2008):86-99]. Thus, in contrast to the present invention, implantation of a spinal cord electrode in the anterior epidural space is considered to be an error, and in any event, the implantation of spinal cord stimulator electrodes is not performed in the lumbar spine (e.g., L3-L5). Furthermore, in the present invention, the electrical stimulus is directed towards the posterior longitudinal ligament in such a way that motor contractions are not induced by the stimulation. Applicant is unaware of the deliberate percutaneous implantation of a spinal cord stimulator in the anterior epidural space. As disclosed herein, such deliberate implantation in the anterior epidural space would likely involve a different anatomical route than the interlaminal approach that is taken for access to the posterior epidural space. Thus, as is known from the methods for performing epidural injections, to reach the anterior epidural space, a transforaminal anatomical approach may be taken, and for lumbar vertebrae, a sacral route may be taken as well [Mark A. HARRAST. Epidural steroid injections for lumbar spinal stenosis. Curr Rev Musculoskelet Med 1:(2008):32-38].

Spinal cord stimulation is performed for the treatment of back pain, but it involves stimulation in vertebrae other than the lumbar spine L3-L5. The vertebral location of the stimulator electrodes is selected on the basis of the location of the patient's pain. BAROLAT et al. mapped the body areas that may be targeted by stimulation of the spinal cord in different vertebrae and made the following observations concerning how best to stimulate to treat lower back pain. "It is very difficult to stimulate the low back only, without intervening chest/abdominal wall stimulation . . . (1) the peak curve for low-back stimulation coincides with the peak curve for the chest/abdominal wall . . . (2) the chest/abdominal wall region has a higher percentage of stimulation than the low back; and (3) the chest/abdominal wall area has a lower stimulation threshold than the low back. All of these factors contribute to the challenge of being able to direct stimulation selectively to the low back without interference from the body walls. In our experience, the best location was about T9-10, with the electrode placed strictly at the midline." [BAROLAT G, Massaro F, He J, Zeme S, Ketcik B. Mapping of sensory responses to epidural stimulation of the intraspinal neural structures in man. J Neurosurg 78(2, 1993):233-9].

It is therefore not surprising that the effectiveness of spinal cord stimulation for lower back pain is equivocal. Most reviews of its effectiveness have been made in connection with the treatment of Failed Back Surgery Syndrome (FBSS), which may involve pain in locations in addition to the back (e.g., the leg). A Cochrane review of random clinical trials for the treatment of FBSS by spinal cord stimulation concluded that although one clinical trial does provide some limited evidence in favor of spinal cord stimulation, the numbers are small and as a result the study fails to achieve statistical significance [MAILIS_GAGNON A, Furlan A D, Sandoval J A, Taylor R. Spinal cord stimulation for chronic pain. Cochrane Database Syst Rev. 2004; (3):CD003783, updated 2009]. Other reviews indicate that up to 40 percent of such FBSS patients do not benefit substantially from spinal cord stimulation [ELDABE S, Kumar K, Buchser E, Taylor R S. An analysis of the components of pain, function, and health-related quality of life in patients with failed back surgery syndrome treated with spinal cord stimulation or conventional medical management. Neuromodulation 13(3, 2010): 201-9; FREY M E, Manchikanti L, Benyamin R M, Schultz D M, Smith H S, Cohen S P. Spinal cord stimulation for patients with failed back surgery syndrome: a systematic review. Pain Physician 12(2, 2009):379-97].

Similarly, a review found that spinal cord stimulation for treatment specifically of discogenic pain might be useful, as evidenced by a reduction in opioid usage by such patients, but the review involved only a small number of patients [VALLEJO R, Manuel Zevallos L, Lowe J, Benyamin R. Is Spinal Cord Stimulation an Effective Treatment Option for Discogenic Pain? Pain Pract. 2011 Jul. 29. doi: 10.1111/j.1533-2500.2011.00489.x. (Epub ahead of print)]. OAKLEY reviews the problem of why approximately 50% of patients with lower back pain are not helped by spinal cord stimulation. He suggests that advances in stimulator technology may help, such as properly selecting the number and location of stimulator electrodes, using pulse generators with independent current control over each lead contact electrode, and optimizing the stimulation waveform (e.g., pulse width) [John C. OAKLEY. Spinal Cord Stimulation in Axial Low Back Pain: Solving the Dilemma. Pain Medicine 7 (Supplement s1, 2006):558-563]. In regards to stimulus waveform optimization, AL-KAISY et al. suggest that the use of high frequency pulses may help [Adnan AL-KAISY, Iris Smet, and Jean-Pierre Van Buyten. Analgesia of axial low back pain with novel spinal neuromodulation. Poster presentation #202 at the 2011 meeting of The American Academy of Pain Medicine, held in National Harbor, Md., Mar. 24-27, 2011].

The above-cited literature demonstrates that the treatment of lower back pain by invasive electrical stimulation is in need of improvement. To that end, the present invention is motivated by the fact that the innervation of the posterior longitudinal ligament and the underlying annulus fibrosus may be the predominant origin of the lower back pain. Thus, KUSLICH et al. write that "... we had the opportunity to perform more than 700 operations on the lumbar spine while using local anesthesia.... Back pain could be produced by stimulation of several lumbar tissues, but by far, the most common tissue of origin [of back pain] was the outer layer of the annulus fibrosus and posterior longitudinal ligament." [KUSLICH S D, Ulstrom C L, Michael C J. The tissue origin of low back pain and sciatica: a report of pain response to tissue stimulation during operations on the lumbar spine using local anesthesia. Orthop Clin North Am 22(2, 1991):181-7].

To affect the innervation of the lumbar posterior longitudinal ligament, the electrodes that stimulate them need to be placed in the lumbar spine, which is not done in spinal cord stimulation for back pain. At that lumbar location, the cauda equina is situated posterior to the posterior longitudinal ligament. Placement of an electrode between the posterior longitudinal ligament and the cauda equina would cause the cauda equina to be stimulated, if the electrode were to stimulate in all directions. Such stimulation of the cauda equina would be very undesirable because it would cause leg movements resulting from stimulation of nerve roots within the cauda equina.

In fact, there are only a few reasons for electrically stimulating the cauda equina, and they are not relevant to the treatment of discogenic back pain. Electrical stimulation of the cauda equina, through high voltage percutaneous or transcutaneous stimulation above the lumbar vertebrae, is sometimes done in order to assess conduction in the cauda equina, which is accompanied by electromyographic activity in muscles of a lower limb. However, this does not involve placement of an electrode in the epidural space [Maertens de NOORDHOUT A, Rothwell J C, Thompson P D, Day B L, Marsden C D. Percutaneous electrical stimulation of lumbosacral roots in man. J Neurol Neurosurg Psychiatry 51(2, 1988):174-81]. Electrodes have been placed in the posterior epidural space in the vicinity of the conus medullaris and cauda equina, but this is done only for purposes of mapping or monitoring, not for the treatment of lower back pain, and not for purposes of stimulating the posterior longitudinal ligament or posterior annulus fibrosus [KOTHBAUER K F, Deletis V. Intraoperative neurophysiology of the conus medullaris and cauda equina. Childs Nerv Syst 26(2, 2010):247-53]. In another situation, a special electrode is used to enable restoration of at least partial control over lower-body functions that are directed by nerves emerging from the end of the spinal cord. The electrode is designed for introduction into the lower end of the dura beneath the conus of the spinal cord, to float in the intrathecal space that is loosely occupied by the sacral roots and other nerves of the cauda equina. Thus, that electrode is not implanted in the epidural space, and it is not intended to treat lower back pain or stimulate the posterior longitudinal ligament or posterior annulus fibrosus [U.S. Pat. No. 4,633,889, entitled Stimulation of cauda-equina spinal nerves, to TALALLA et al].

Therefore, if one wishes to electrically stimulate the lumbar posterior longitudinal ligament to treat back pain reversibly, but avoid stimulation of other structures adjoining the anterior epidural space, at least two problems must be addressed. One is that the electrical stimulation must be directed specifically to the posterior longitudinal ligament and its underlying structures, and this involves not only designing an asymmetric structure for the lead, but also the design of directionality of its insertion into the patient. A second problem is that electrodes, particularly percutaneous electrodes (wire, or catheter-like electrodes) have a tendency to migrate or rotate, such that even if the electrode were initially directed to stimulate the posterior longitudinal ligament, it may eventually rotate or migrate, thereby accidentally stimulating other tissues. The present invention is designed to address both of these problems. It also addresses the problem of selectively ablating the nerves if the reversible stimulation does not work.

These problems are not addressed in the patents that are related to the present invention. In U.S. Pat. No. 7,069,083, U.S. Pat. No. 7,831,306, and U.S. Pat. No. 8,086,317, all entitled System and method for electrical stimulation of the intervertebral disc, to FINCH et al., a percutaneous (wire, or catheter) lead is placed in a disc or just outside the outer confines of the disc, circumferentially along the entire perimeter of the annulus of the disc. The lead is not placed in the anterior epidural space, there is no suggestion of stimulating the posterior longitudinal ligament, the electrodes do not stimulate in a particular direction, and there is no suggestion of how rotational migration of its cylindrical lead might be retarded. In U.S. Pat. No. 7,945,331, entitled Combination electrical stimulating and infusion medical device and method, to VILIMS, it is suggested incidentally that his disclosed percutaneous (wire, or catheter) lead "is well suited for treatment of other areas along the spine to include the ventral canal along the posterior longitudinal ligament, ventral dura, and the posterior aspect of the disc." However, there is no suggestion as to how the lead would be inserted or used in those locations. In one embodiment of that invention, "the electrodes are not formed circumferentially around the distal portion, but are formed more linearly along one side of the stimulation lead." However, that patent does not suggest how such an electrode would be inserted to selectively stimulate any particular tissue, and it does not suggest how subsequent rotational migration of its cylindrical lead could be retarded. Furthermore, that patent is concerned with managing sacroiliac joint pain in a sacrum of a patient, not discogenic lumbar pain. None of the above-cited patents disclose devices that would almost completely cover a pain-generating region, such as the entire innervation of an offending lumbar posterior longitudinal ligament and adjacent posterior annulus fibrosus of the intervertebral disc(s).

In view of the foregoing, there is a need for a lumbar vertebral column electrical stimulator lead that is adapted for directional insertion into the anterior epidural space adjacent to the posterior longitudinal ligament; that will provide adjustable and reversible non-destructive modulation of nerves in the posterior longitudinal ligament and underlying annulus fibrosus to effectively reduce back pain, when connected to a pulse generator; that will cover the pain-generating region; that will stimulate only the posterior longitudinal ligament and underlying annulus fibrosus, but not nearby tissue such as the cauda equina or nerve roots; that is not susceptible to accidental rotation or migration; and that as a last resort may be used to irreversibly damage the offending nerves, without the use of thermal ablation that indiscriminately damages material near the offending nerves, such as collagen in the posterior longitudinal ligament.

SUMMARY OF THE INVENTION

The present invention is directed to methods and devices for the treatment of chronic lower back pain that may result from a degenerated or injured intervertebral disc.

An array of electrodes, along with a pulse generator that is connected to the electrodes, are used to deliver electrical impulses to nociceptive and/or other nerves located within the posterior longitudinal ligament of the lumbar spine and the outer posterior annulus fibrosus of the intervertebral disc(s) that lies adjacent to the posterior longitudinal ligament.

According to the invention, the electrical stimulation in this region may reduce back pain in a patient reversibly, adjustably, and with almost complete coverage of the pain-generating region, for example, by interfering with or modulating afferent pain signals to the brain that originate in those nerves. Alternatively, if the reversible electrical stimulation is unsuccessful in alleviating the back pain, electrical stimulation parameters may be selected so as to irreversibly damage the ability of the nerves to send pain signals to the brain, using irreversible electroporation. All stimulating electrodes are unidirectional, such that the electrodes are located on one side of the insulating material to which they are attached, e.g., a flexible, inert silicone elastomer (such as Silastic™) or similar flexible material, to prevent electrical stimulation to the overlying thecal sac and the nerves contained therein.

Implantation of the stimulator electrodes may involve a two-step process. A temporary array of electrodes (a lead) may first be implanted transcutaneously and attached by wires to an external (nonimplanted) pulse generator. One or more of such leads are inserted for the trial under sterile conditions under local anesthesia, with or without conscious sedation. The temporary leads have electrodes that are disposed linearly along a side of the lead. The temporary leads are straight and thin, as compared to the permanent leads that may subsequently be implanted, in order to facilitate transcutaneous implantation of the temporary leads. Although temporary leads may be placed longitudinally or horizontally, horizontal placement at one or more vertebral levels via a transforaminal approach will be most common. For implantation of the temporary leads, epidurography is used in order to see that the cauda equina and nerve roots are safely negotiated. Whether the lead is temporary or permanent, its implantation is accompanied by intra-operative electrophysiologic monitoring (somatosensory-evoked potential measurement, spontaneous or triggered electromyography, etc.) to assess the functional integrity of the cauda equina and nerve roots and to detect if that functional integrity is compromised during insertion and/or stimulation of the lead(s).

Because of the potential danger of accidentally stimulating the thecal sac and nerves contained therein, the temporary lead is specially designed to prevent accidental rotation of electrodes of the lead towards the thecal sac. The sides of the lead preferably comprise fins that protrude from the main body of the lead which, when inserted into the tissue of the anterior epidural space, will prevent rotation and migration of the leads. Furthermore, although the body of the temporary lead may be shaped in a conventional catheter-like cylindrical form, a flat shape with a rounded or curved tip is preferable in order to prevent rotation and to maintain directionality of electrodes of the lead toward the PLL. In order to implant such flat and/or finned leads into a suitable position, special percutaneous implantation methods and devices are used. Intraoperative electrophysiological monitoring is also used to confirm that the thecal sac is not being damaged or stimulated by a lead, either during the lead's insertion or when electrical pulses are applied to the lead.

If stimulation of the temporary electrodes is successful in reducing back pain, a permanent array of electrodes is implanted and attached by wires to an internal (implanted) pulse generator. The permanent electrodes are generally disposed nonlinearly across the surface of a paddle lead (plate lead or surgical lead). The direction and route of permanent electrode insertion may be chosen based on the implanter's preference and the extent of the pain generating region. The objective is for the electrodes to cross the path of nerves identified as the stimulation target. The permanent paddle leads are specially designed to contour the posterior vertebral column, such that the surface area of the contact electrodes narrows in those regions bound by two pedicles. This configuration also aids in anchoring the leads in place. Similar to temporary leads, permanent leads may be placed horizontally along the width of the posterior annulus of an intervertebral disc and overlying PLL or placed longitudinally along the PLL that spans the distance between one or more intervertebral discs. The length and width of the electrode paddle leads will vary to accommodate the corresponding dimensions of the pain-generating region as measured on CT or MRI in individual patients. If the reversible electrical stimulation is not successful in alleviating the pain, the lead may also be used to damage the nerves irreversibly, wherein non-thermal electroporation produces the damage. In a different embodiment, the device may be used to relieve pain in the patient by irreversibly damaging nerves in the posterior longitudinal ligament and/or posterior annulus fibrosus by joule heating and/or by dielectric heating of proteins, wherein a thermal insulator covers substantially all of the cauda equina or thecal sac, thereby shielding the cauda equina or thecal sac from the heat that could cause damage.

Considered as a system, the invention comprises the following components:
1) Specially designed temporary leads (percutaneous type with linearly arranged electrodes) and permanent leads (paddle leads with generally nonlinearly arranged electrodes), with the electrodes situated in a flexible, inert silicone elastomer (such as Silastic™) or similar flexible insulating material, wherein electrical pulses are transmitted from the electrodes to adjacent tissue unidirectionally.

2) Pulse generators designed for internal (implanted) and for external use that transmit electrical pulses to the electrodes via wires, and a programmer that controls the pulse generator. The programmer is used to adjust each electrode's electrical pulse rate, duration, amplitude and anode/cathode configuration, as well as each electrode's state of connection or disconnection to the pulse generator. The programmer may provide control signals to the pulse generator using radiofrequency or infrared transmission, and it may also provide power to the pulse generator if the pulse generator is not powered by batteries.

3) Specially designed surgical aides for implantation of the leads, such as a trocar, obturator, stylet, lead blank, introducer cannula, anchoring tabs, and tools used for connecting the electrodes to the pulse generator.

However, it should be understood that application of the methods and devices is not limited to the examples that are given. The novel systems, devices and methods for treating conditions using the disclosed stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 5 shows a percutaneous flat lead and a pulse generator that may be used to stimulate nerves in the posterior longitudinal ligament and underlying annulus fibrosus, according to the present invention. In FIG. 5A, the lead is shown to be a percutaneous flat lead, and in FIG. 5B, a directional indicator is shown to point in the correct direction when the lead has been inserted correctly.

FIG. 6 shows methods and devices for inserting the percutaneous lead of FIG. 5 into the anterior epidural space of a patient. Entry into that space for the L4-L5 disc is shown in FIGS. 6A and 6B, in a side view and in a posterior view, respectively.

FIG. 7 shows exemplary paddle leads that may be used to stimulate nerves in the posterior longitudinal ligament and underlying annulus fibrosus, according to the present invention. The lead shown in FIG. 7A is intended to be placed horizontally within the anterior epidural space, and the lead shown in FIG. 7B is intended to be placed vertically (longitudinally) within the anterior epidural space.

DETAILED DESCRIPTION OF THE PREFERRED EMBODIMENTS

Figure 1:
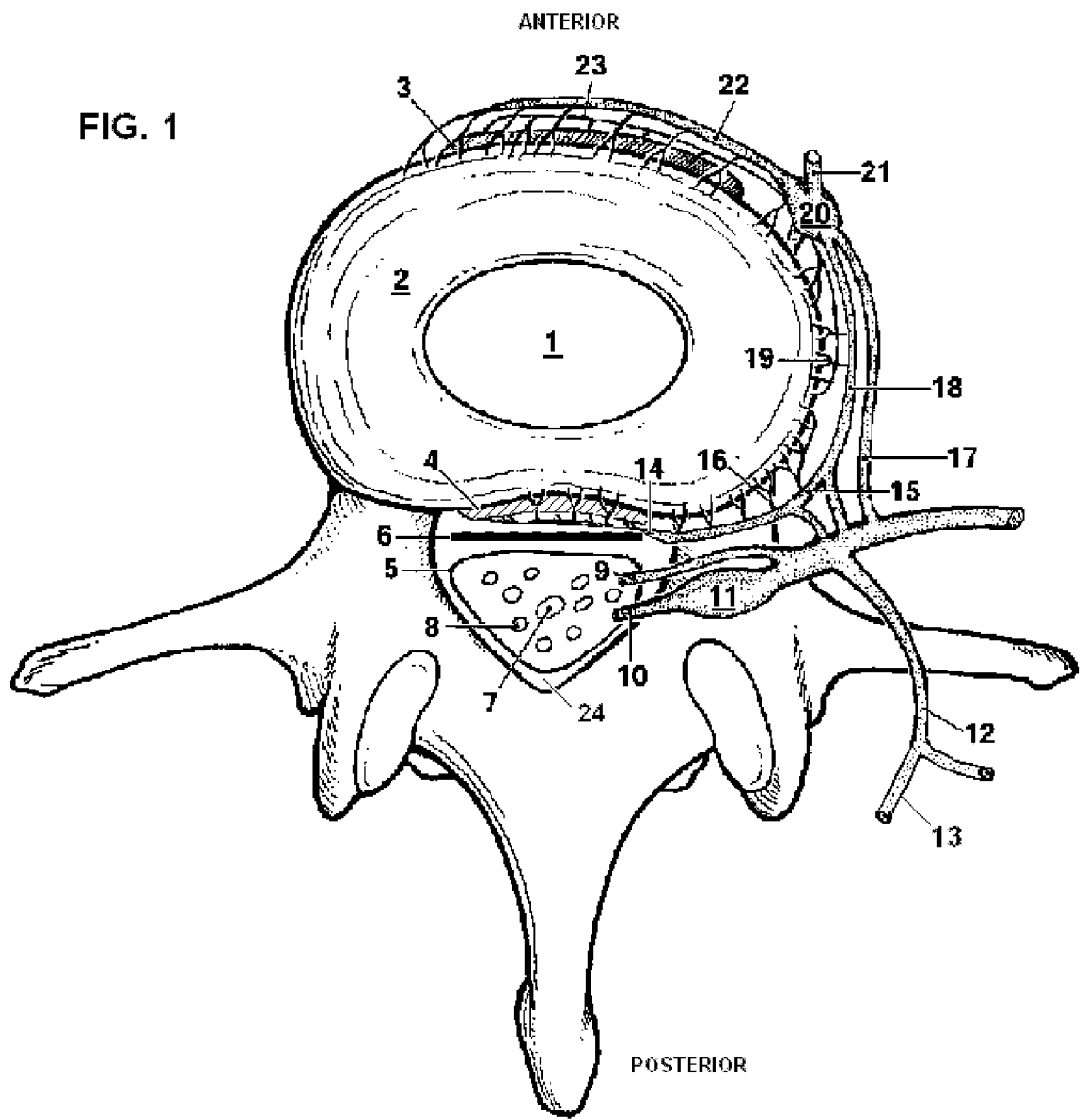
FIG. 1 shows the spine in a cross section perpendicular to its long axis, cut through one of the lumbar discs.
Figure 2:
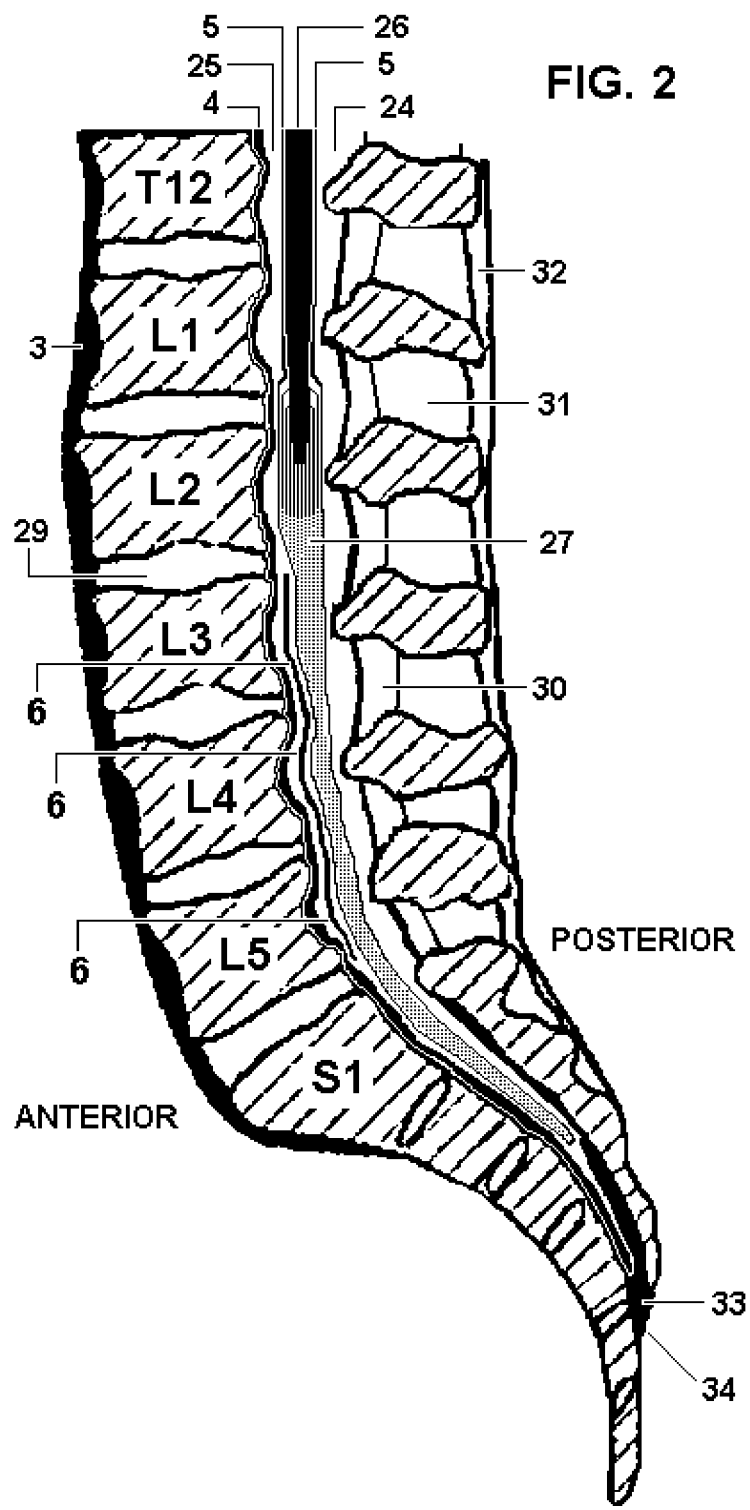
FIG. 2 shows a cross section of the lumbar spine viewed from the side (left-to-right).

FIG. 5 shows an array of electrodes and a pulse generator that may be used to stimulate nerves in the posterior longitudinal ligament and underlying annulus fibrosus, according to the present invention. An array of electrodes is also known as a lead. In FIG. 5A, the lead 60 is shown to be a percutaneous flat lead. The width of the lead may be, for example, 0.5 cm. As shown, it contains eight contact electrodes 61, which are embedded in insulating material 62. For example, the contact electrodes may be made of an alloy of platinum/iridium, and the insulation material may be made of a flexible, inert silicone elastomer (such as Silastic™), polyurethane or silicone/polyurethane. When the lead is rotated by 90 degrees and sectioned along its axis, wires 63 are seen to connect each contact to corresponding connection points in the Pulse Generator 64. The wires 63 may also be embedded in the insulating material 62. For example, the wires may be made of the conducting material 35NLT-DFT-28% Ag or MP35N-DFT-28% Ag. The pulse generator 64 may be powered by batteries, or it may be powered by a radio-frequency driven passive receiver. If the pulse generator is implanted in a patient, it may be programmed through an external transmitter.

When the lead 60 is rotated by 180 degrees to show its back side, the contact electrodes 61 are no longer visible. Instead, the locations above the contact electrodes (shown with dotted lines) are covered by insulating material. Consequently, stimulation with the lead 60 occurs preferentially on one of its sides, namely, the side with exposed contact electrodes 61.

For the invention to function properly, the exposed electrodes 61 should face the posterior longitudinal ligament. This is because it is intended to stimulate nerves in the posterior longitudinal ligament and underlying annulus fibrosus but avoid stimulating other tissue such as the thecal sac. To assist in confirmation that the lead is oriented properly when inserted into the patient, the lead contains one or more radio-opaque directional indicator 65 that may be visualized using fluoroscopy. As shown in FIG. 5B, the directional indicator 65 will point in the correct direction when the lead has been inserted correctly. The insertion of the lead may be horizontal along the intervertebral portion of the PLL 66, or it may placed vertically (longitudinally) along the vertebral portions of the PLL 67, or both. In fact, in addition to the horizontal lead at the L4/L5 disc location, another horizontal lead may be inserted at the L3/L4 disc location or other locations. The vertical lead 67 is shown in FIG. 5B to contain sixteen contact electrodes, which will connect to sixteen corresponding connection points in the pulse generator, but otherwise the longer sixteen-contact lead functions like the shorter eight-contact lead. Other items labeled in FIG. 5B are intervertebral fibers of the posterior longitudinal ligament 48, vertebral fibers of the posterior longitudinal ligament 49, and pedicles (cut) 40.

The percutaneous lead could be cylindrical or, preferably, flat. For purposes of defining flatness, consider a cross section of the lead perpendicular to the long axis of the lead. If that cross section can be represented by about four or fewer connected straight lines and at most one curved line, then the lead is flat along the surface containing the longest straight line. For example, the lead may be rectangular in cross section perpendicular to its long axis, with one side of the rectangle being potentially much longer than its adjacent sides (as in a strap). In either case, it is preferred that the lead will have attached fins 67 (which may also be called wings) that inhibit movement or rotation of the lead from its preferred orientation. For example, FIG. 5B shows such a preferred lead orientation. For present purposes, a fin is defined to be something that resembles a fin in appearance, function, or position relative to the main body of the electrical lead. The preferred embodiment of the lead having fins is most useful when used with methods that are disclosed below in connection with FIG. 6 for inserting and orienting the lead in the patient. The fins 67 are shown in FIG. 5A in the positions that they naturally attain when they are free to move. However, it is understood that the fins 67 are also sufficiently flexible that they may be temporarily bent, approximately flat against the main body of the lead, when the lead with attached fins is inserted into the slightly larger diameter lumen of a needle, cannula, or catheter. Fins have previously been attached to stimulator leads, but not as in the present invention. In U.S. Pat. No. 6,654,644, entitled Pacemaker electrode, to SANCHEZ-ZAMBRANO, a fin is given a serrated edge to facilitate its removal from cardiac tissue. In U.S. Pat. No. 7,894,913, entitled Systems and methods of neuromodulation stimulation for the restoration of sexual function, to BOGGS et al, a fin comprising non-conductive material is shown to focus (reflect) electrical stimulation energy toward a targeted tissue region and away from a non-targeted tissue region. However, in the present invention, the focusing of electrical stimulation is due to the arrangement of electrodes along one side of the lead, not to the presence of the fins. Furthermore, the fins along the side of the lead of the present invention could in principle be made of conducting material, for example, material containing heavy metals that are radio-opaque, which would facilitate imaging of the fins with fluoroscopy. The characteristics of the fins most relevant to the present invention are that the fins should be flexible enough to be temporarily bent during passage through a needle or cannula, but strong enough in the unbent state to withstand rotation when inserted into the anterior epidural space of the patient.

Anatomical considerations related to insertion of a percutaneous lead of the present invention are as follows. A venous plexus surrounded by various amounts of fat almost entirely fills the anterior epidural space. In the thoracolumbar region (T10-L2) the basivertebral vein originates from this venous plexus and extends into the vertebral bodies. As the size of the dural sac relative to the epidural space decreases at the L4-L5 level, the anterior dura falls away from the posterior longitudinal ligament, and fat fills the anterior epidural space. Therefore, the insertion of a lead into the midline of the anterior epidural space will likely encounter decreasing mechanical resistance as one proceeds from L2 to L5. Consequently, if a percutaneous lead is inserted in the vertical (longitudinal) direction, the preferred direction may be from L5 to L3, as shown in FIG. 5B. Depending on the need to change the direction of the distal end of the lead during its insertion, the lead may also be inserted through a needle or cannula having a tip that produces deflected movement of a wire or some other linear element that is inserted through the needle.

Percutaneous entry into the anterior epidural space is accomplished by a transforminal route, or possibly a caudal approach via the sacral hiatus in the case of leads inserted longitudinally. Another possible percutaneous entry route, albeit less likely, is the posteriorlateral interlaminal approach, especially at the level of L5 and S1 for longitudinal lead placement. Percutaneous entry to the anterior epidural space is performed under fluoroscopic guidance, for example in the transforaminal approach, wherein a needle is positioned within a safe zone of the intervertebral neural foramen, most commonly within a region just lateral and cephalad to the margin of the inferior pedicle, dorsal to the vertebral body and caudal to the nerve root (Kambin's triangle), taking care to avoid damage to the nerve root. Endoscopic guidance may also be used in this and subsequent implantation steps.

The entry is shown in FIGS. 6A and 6B. Labels in those figures correspond to: Touhy epidural needle 70, anterior epidural space 25, L3 nerve root 35, L4 nerve root 36, L5 nerve root 37, thecal sac 5, and L4-L5 left neural foramen 71. Fluoroscopic contrast agents will ordinarily be injected to traverse the epidural space and outline the dorsal root ganglion, nerve root, and thecal sac, thereby making it possible to visualize a safe insertion of the needle into the anterior epidural space [JOHNSON B A, Schellhas K P, Pollei SR. Epidurography and therapeutic epidural injections: technical considerations and experience with 5334 cases. AJNR Am J Neuroradiol 20(4, 1999):697-705]. A posterolateral approach is an alternative to the conventional transforaminal approach, in cases where needle tip positioning in the anterior epidural space is difficult [I. S. LEE, S. H. Kim, J. W. Lee, S. H. Hong, J.-Y. Choi, H. S. Kang, J. W. Song, and A. K. Kwon. Comparison of the temporary diagnostic relief of transforaminal epidural steroid injection approaches: conventional versus posterolateral technique. American Journal of Neuroradiology 28 (2007): 204-208].

More specifically, a scalpel is used to make a small incision where the epidural needle will enter the skin. Under fluoroscopy, a Touhy (or similar) epidural needle is inserted as shown in FIG. 6. Entry into the epidural space is confirmed by the ability to blow air into it due to negative pressure within the epidural space. Fluoroscopic contrast agents may be used at this point to assess the location of the tip of the needle relative to the pertinent anatomy such as the nerve root, pedicles, and edge of the thecal sac. A guide wire is then inserted into the lumen of the needle and positioned at the border of the anterior thecal sac and underlying PLL. The needle is then withdrawn, leaving the guide wire in place. A rigid introducer cannula is placed over the guide wire and docked on bone just lateral to the anterior edge of the thecal sac where it meets the posterior spinal column. A flexible introducer cannula may also be used instead. Alternatively, an obturator may be placed in the central opening of the introducer cannula and around the guide wire during initial advancement of the introducer cannula to prevent potential blockage of its lumen by tissues. Once the obturator is removed, fluoroscopic contrast dye can again be used, administered through the cannula, to confirm proper placement of the tip of the cannula. The shape of the cannula and the shape of its lumen is designed to accommodate the shape of the lead: round to accommodate a rounded catheter-like lead and rectangular to accommodate a flat lead which is preferable. The orientation of the tip or bevel of the introducer cannula is known by corresponding markings on the handle of the cannula. Consequently, the orientation of the tip of the cannula and handle is known with respect to the orientation of the lead, once the lead is delivered through the cannula in the desired orientation (i.e., with the electrodes directed downward towards the posterior vertebral column). Once the cannula is confirmed to be in the proper position, the lead can be delivered through the cannula and advanced under fluoroscopy into the anterior epidural space and across the posterior vertebral column, again, making sure that the electrode contacts are directed towards the PLL and away from, or opposite, the thecal sac.

If problems arise in advancing the lead into the anterior epidural space, the route of the lead to its desired final position in the epidural space may be opened (tunneled). In one embodiment of the invention, a flexible lead blank used as a trocar may be passed through the cannula into the anterior epidural space to create a passageway for the placement of the lead. The lead blank is preferably made of a flexible alloy such as Type 304 stainless steel with barium sulfate to make it radio-opaque. The tip of the lead blank is rounded like the true lead to prevent puncturing of the thecal sac during the tunneling process. Once the lead blank has successfully tunneled across the posterior vertebral column in the anterior epidural space, it can be removed and the lead can then be passed into place through the introducer cannula as described above. An alternative method of delivering a temporary lead, especially one with a greater width than 0.5 cm, may include the use of multiple cannulas, each with a larger lumen size than the others, introduced in succession (i.e., one over the other), until the desired lumen size will accommodate the desired electrode lead width. The outside and lumens of such cannulas may have cross-sectional shapes that are not circular (e.g., rectangular). This alternative method may or may not involve the use of a Touhy (or similar) epidural needle and/or guide wire.

Intra-operative electrophysiologic monitoring is performed in order to assure that the lead has not been inserted in the wrong direction and is not defective [Thomas N. PAJEWSKI, Vincent Arlet and Lawrence H. Phillips. Current approach on spinal cord monitoring: the point of view of the neurologist, the anesthesiologist and the spine surgeon Eur Spine J 16(Suppl 2, 2007): 115-129; MALHOTRA, Neil R and Shaffrey, Christopher I. Intraoperative electrophysiological monitoring in spine surgery. Spine 35(25, 2010):2167-2179]. Preliminary electrical stimulation is then performed to test operation of the stimulator, confirming that there are no motor responses on the part of the patient at low stimulation voltages. With the lead in place, the introducer cannula is then fully removed. The lead is subsequently secured in place, e.g., by attaching to the patient's skin or possibly to an interspinous ligament. Alternatively, an anchor is used to secure the lead (e.g., U.S. Pat. No. 7,899,553, entitled Lead anchor for implantable stimulation devices, to BARKER). With the lead attached to the pulse generator, the pulse generator is now ready to be programmed to obtain a reduction in back pain, as described below.

If a percutaneous lead like the ones shown in FIG. 5 is successful in reducing the patient's back pain after a trial period of typically one or two weeks, replacement of that lead with one capable of simulating a larger surface area would be warranted [NORTH R B, Kidd D H, Olin J C, Sieracki J M. Spinal cord stimulation electrode design: prospective, randomized, controlled trial comparing percutaneous and laminectomy electrodes-part I: technical outcomes. Neurosurgery 51(2, 2002):381-9]. Such a larger area can be covered by electrodes mounted in a paddle lead (also known as a plate or surgical lead). Two exemplary paddle leads are shown in FIG. 7. The lead shown in FIG. 7A is intended to be placed horizontally within the anterior epidural space, across one of the patient's discs and across nerves within intervertebral fibers of the posterior longitudinal ligament. The lead shown in FIG. 7B is intended to be placed vertically (longitudinally) to stimulate nerves in vertebral fibers of the posterior longitudinal ligament, as well as portions of two (or more) of the patient's discs and intervertebral fibers of the PLL.

Apart from the fact that electrodes in the percutaneous lead shown in FIG. 5 are arranged linearly, which is in contrast to the electrodes in the paddle leads shown in FIG. 7 that are disposed non-linearly across the surface of the lead, the construction of the percutaneous and paddle leads are similar. In particular, all stimulating electrodes 61 of the paddle leads are unidirectional, such that the electrode contacts are located on one side of the insulating substrate of the paddle 62 that is made of a flexible, inert silicone elastomer (such as Silastic™) or similar material, to prevent stimulation to the overlying thecal sac and the nerves therein. It is advantageous to use a somewhat elastic insulating substrate, in order to accommodate changes in the geometry of the discs that accompany flexion and extension [PEARCY M J, Tibrewal S B. Lumbar intervertebral disc and ligament deformations measured in vivo. Clin Orthop Relat Res (191, 1984):281-6].

Thus, the electrode contacts in FIG. 7A are visible in the view 95. When that view is rotated by 90 degrees, as in the view labeled as 96, a cross section of that rotated view would reveal the electrodes 61, wires 63 that connect the electrode to a pulse generator (64 in FIG. 5), and channels 97 through which those wires run. When the view 95 is rotated by 180 degrees to produce the view labeled as 98, the electrodes are no longer visible. Thus, only the insulating material may be seen from that back side (underlying electrode locations are indicated with dotted lines). The view labeled as 98 also shows how the lead is placed horizontally across one of the patient's discs and across nerves in the intervertebral fibers of the posterior longitudinal ligament and annulus fibrosus, within the anterior epidural space. Radio-opaque directional indicators 65 are also shown to be located within the leads, allowing the orientation of the lead to be visualized by fluoroscopy. Such directional indicators may be redundant if the arrangement of electrodes across the lead is not symmetrical, in which case, the electrodes themselves may also serve as directional markers.

As shown in FIG. 7B, a longitudinal (or vertical or vertebral) lead will widen at the disc spaces to accommodate the posterior lateral margins of the annulus fibrosus. Such permanent paddle electrodes are specially designed to contour the posterior vertebral column so that the surface area of the contact electrodes narrows in those regions bound by two pedicles. This anatomical consideration applies to the horizontal lead shown in FIG. 7A, as well as to the longitudinal lead shown in FIG. 7B. This configuration also aids in anchoring the leads in place. The lead shown in FIG. 7B is shown to contain 32 electrode contacts because it covers a larger surface area than the lead shown in FIG. 7A (with 16 electrode contacts). The length and width of the paddle leads will vary to accommodate the corresponding dimensions of the lumbar discs as measured using CT or MRI imaging. The width of the electrode paddles will be limited to some extent by the distance between two adjacent nerve roots, as estimated from the location of pedicles 40. Thus, the paddle electrodes shown in FIG. 7 differ from presently available spinal cord paddle leads in that the leads of the present invention should be custom fit for each patient (at least within a narrow range of dimensions), otherwise the leads will not fit into the patient properly. The distance between two adjacent ipsilateral nerve roots should approximate the ipsilateral interpedicular distance 100 (1.5-2.5 cm), which is slightly less than the contralateral interpedicular distance (2.0-3.0 cm) that varies according to the particular vertebra: 2.0-2.2 cm for L3 101, 2.2-2.6 cm for L4 102, and 2.6-3.0 cm for L5 103). The space limitation created by the distance between two adjacent nerve roots may warrant two leads to be placed side by side in rare cases requiring wider coverage. The longitudinal (or vertical) lead length 104 will vary depending on the extent and number of discs to be included in the stimulated area (typically 6.0 to 8.0 cm to achieve a distance that spans from L3-L4 to L4-L5 and 8.0 to 9.0 cm if extension from L3-L4 to L5-S1 is required). For comparison, the maximum length of the horizontal lead shown in FIG. 7A will be approximately the distance measured from one side of an intervertebral disc to the other 105 (4.0-5.0 cm), and in the perpendicular direction, the width of the horizontal lead will be approximately the thickness or height of an intervertebral disc 106 (approximately 1.0 cm).

The permanent leads contain small tabs 99 that are used to anchor the lead to bone or other relatively immobile tissue such as the annulus fibrosus, e.g., wherein sutures are passed through the tabs. The electrical connection going from the lead to the pulse generator can be situated at the end of the electrode paddle 108 or on the side of the paddle 109 to accommodate the most suitable region of access for electrode placement.

Figure 3:
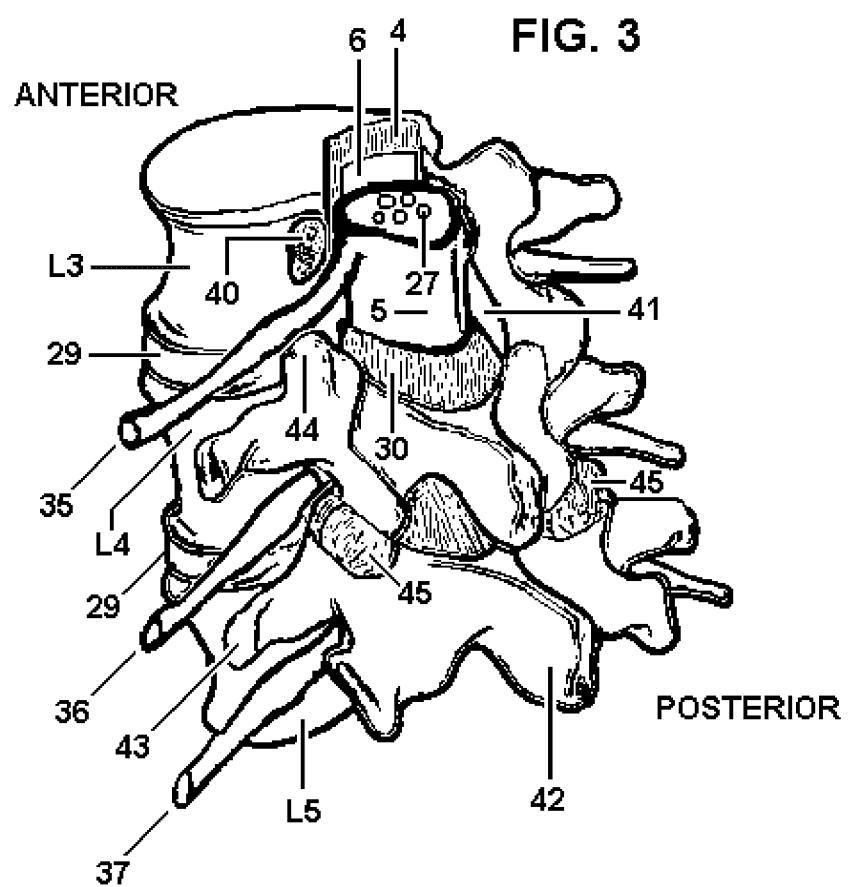
FIG. 3 shows a posterior-to-anterior view of the lumbar spine, viewed obliquely on the left side of the patient.

Direct access to the region via a standard laminotomy or laminectomy approach may be used to insert the paddle lead. Thus, a small window of bone (laminotomy) is drilled over the area using minimally invasive techniques to allow insertion of the electrodes into the epidural space. Other times, more bone must be removed (laminectomy) to allow safe and accurate placement of the electrodes. Such an approach may be accomplished using a minimally invasive or open technique. The laminotomy may be performed, for example, by removing lamina (41 in FIG. 3) of vertebrae L4 and L5, or alternatively between L5 and 51. As an example, the initial steps of Technique 39-20 and its FIG. 39-37 in WILLIAMS and PARK describe a method for gaining access to the anterior epidural space, into which the lead is inserted [Keith D. WILLIAMS and Ashley L. Park. Lower Back Pain and Disorders of Intervertebral Discs. Chapter 39, pp. 2159-2236. In: Campbell's Operative Orthopaedics, 11th edition (S. Terry Canale and James H. Beatty, eds). Philadelphia: Mosby Elsevier, 2007]. A full laminectomy involving one or more levels may also be required in cases in which significant central canal stenosis does not allow adequate space within the anterior epidural compartment to accommodate lead placement. Once placed in the desired location, the lead is then anchored or sutured to firm and relatively immobile tissue or bone to prevent migration or displacement. Because the paddle lead has an extensive flat surface, rotation of the lead is not an issue, and placement of the lead with its electrodes facing the posterior longitudinal ligament (and its insulating back towards the thecal sac) will prevent stimulation of the thecal sac. However, if there is some non-rotational migration of the lead, a snare method may be used to reposition the lead [MACDONALD J D, Fisher K J. Technique for steering spinal cord stimulator electrode. Neurosurgery 69(1 Suppl Operative, 2011):ons83-6]. The paddle lead may be inserted using an adaptation of the devices described above in connection with the temporary lead, or tools otherwise used for disc surgery may be used, adapted for operation in the anterior epidural space rather than the disc itself [U.S. Pat. No. 6,830,570, entitled Devices and techniques for a posterior lateral disc space approach, to FREY et al]. Once the paddle lead is secured in place, wires from the lead are attached to the pulse generator, and the pulse generator is ready to be programmed to obtain a reduction in back pain, as now described.

The stimulator leads are connected with wires to a pulse generator (implanted or external) that is similar to the ones used for spinal cord stimulation. Examples of such pulse generators are found in U.S. Pat. No. 7,979,126, entitled Orientation-independent implantable pulse generator, to PAYNE et al; U.S. Pat. No. 7,949,393, entitled Implantable pulse generator comprising fractional voltage converter, to VARRICHIO et al; and U.S. Pat. No. 7,930,030, entitled Implantable pulse generator having current steering means, to WOODS et al. Parameters of the pulses that are generated by the pulse generator are selected using a programmer. Examples of programmers are found in U.S. Pat. No. 6,622,048, entitled Implantable device programmer, to MANN et al; U.S. Pat. No. 6,249,703, entitled Handheld patient programmer for implantable human tissue stimulator, to STANTON et al; U.S. Pat. No. 7,359,751, entitled Clinician programmer for use with trial stimulator, to ERICKSON et al; and U.S. Pat. No. 7,738,963, entitled System and method for programming an implantable pulse generator, to HICKMAN et al. Power to the pulse generator is ordinarily from a fully implantable battery, or alternatively from a radiofrequency system, wherein the power is transmitted through the skin by closely applied transmitting coils [U.S. Pat. No. 3,727,616, entitled Electronic system for the stimulation of biological systems, to LENZKES]. As described by LENZKES, the pulse generator may also be programmed via radiofrequency signaling that controls the activation, intensity, distribution, and frequency of electrode stimulation.

The exemplary pulse generator 64 in FIG. 5A shows that each of the electrodes of a lead may be programmed to be either disconnected or connected to the pulse generator. If the electrode is connected, the pulse generator may in principle vary the voltage of each electrode independently, considering the external case of the pulse generator to be a point of voltage reference. In principle, many types of waveforms may be impressed by the pulse generator upon an electrode [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. Unlike spinal cord stimulation, the stimulation of the present invention may be performed first with successive small subsets of the electrodes of the lead (e.g., 1 electrode, or 2 or 3 adjacent electrodes), in order to locate the underlying nerves that are causing the back pain. Such a mapping will aid in the subsequent programming of the pulse generator, and it may also be useful for identifying where to ablate nerves in the event that reversible stimulation is not successful. This is not to say that the cumulative pain experienced by the patient is necessarily the simple summation of the pain emanating from individual nerves, because the pain signals from individual nerves may interact with one another to produce greater or lesser pain signals than those from nerves individually. Therefore, the stimulation of small subsets of electrodes of the lead may be followed by simultaneous stimulation of pairs of such subsets, in order to also map the interactions between the underlying nerves.

If the pulse generator is like the ones conventionally used for spinal cord stimulation, it will provide rectangular, biphasic, charge-balanced pulses of adjustable rate and duration to each electrode. For the conventional pulse generator, all electrode contacts connected as anodes will have the same voltage, and all electrode contacts connected as cathodes will have the same voltage. Unipolar stimulation can be applied only if the case of the pulse generator is used as a distant anode. Thus, each electrode is conventionally programmed to have one of three states: disconnected, anode, or cathode [DE VOS C C, Hilgerink M P, Buschman H P, Holsheinner J. Electrode contact configuration and energy consumption in spinal cord stimulation. Neurosurgery 65(6 Suppl, 2009): 210-6]. The states V1, . . . , V8 in the pulse generator 64 in FIG. 5A represent those states.

Figure 4:
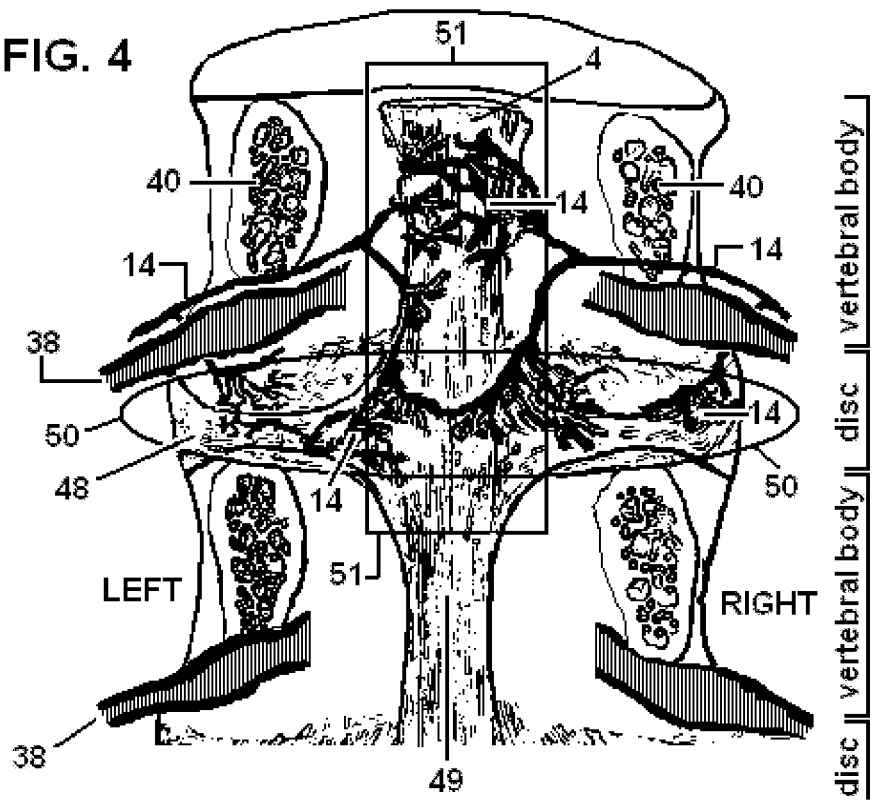
FIG. 4 shows a posterior-to-anterior view of the innervation of the posterior longitudinal ligament (PLL) and of the annulus fibrosus of the intervertebral disc that lies adjacent to the PLL.
Figure 8:
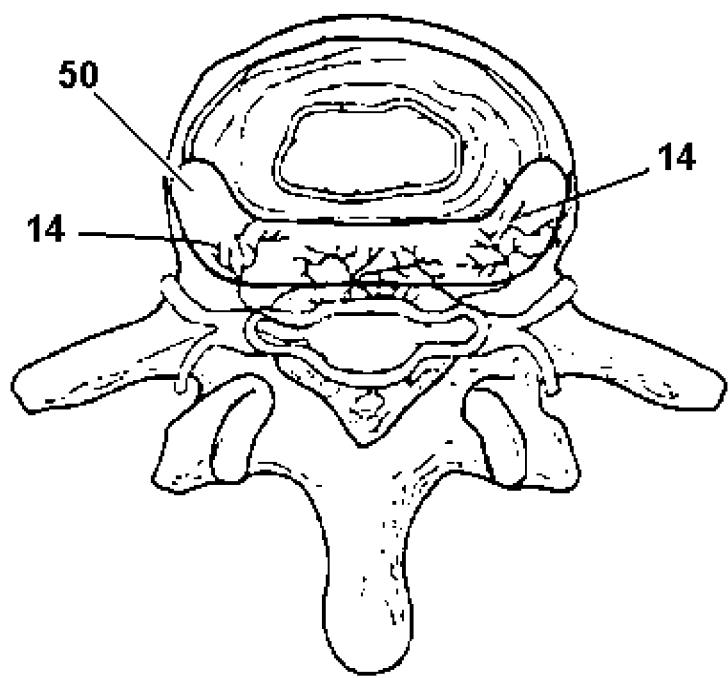
FIG. 8 shows a preselected target volume to be electrically stimulated according to the present invention, wherein the volume is chosen to include nerves of the posterior longitudinal ligament and underlying annulus fibrosus.

As noted above, programming of the pulse generator may be aided by preliminary stimulation involving successive small subsets of the electrodes of the lead, in order to locate the underlying nerves that are causing the back pain. More generally, for a lead containing 16 or 32 electrodes, the number of possible programmed states is very large, in which case, the selection of the programmed state is preferably done with the aid of computer simulation [HOLSHEIMER J. Computer modelling of spinal cord stimulation and its contribution to therapeutic efficacy. Spinal Cord 36(8, 1998):531-40]. For the present invention, the modeling incorporates knowledge of the electrical properties of the disc and its surrounding tissue [GU W Y, Justiz M A, Yao H. Electrical conductivity of lumbar annulus fibrosus: effects of porosity and fixed charge density. Spine 27(21, 2002):2390-5]. Pulse width is usually set to between 100 to 400 microseconds, but for such modeling, the pulse width is also a variable, which affects the area of coverage [LEE D, Hershey B, Bradley K, Yearwood T. Predicted effects of pulse width programming in spinal cord stimulation: a mathematical modeling study. Med Biol Eng Comput 49(7, 2011):765-74]. The result of the simulation is a set of programming options, selected to preferentially stimulate nerves in a preselected target volume. This is shown in FIG. 8, where 50 is the preselected target volume, which is chosen to include the nerves 14 that are to be stimulated (also shown in FIG. 4). After an initial electrode configuration is selected, the configuration may be reprogrammed to optimize its effectiveness, even after the lead is implanted in the patient [MANOLA L, Holsheinner J, Veltink P H, Bradley K, Peterson D. Theoretical investigation into longitudinal cathodal field steering in spinal cord stimulation. Neuromodulation (2, 2007):120-32].

The amplitude of the pulses is typically chosen to be between 0 and 10 V and is set to the smallest value that significantly reduces back pain. Generally, pain relief will be experienced between 2 and 4 V, but this depends on the electrodes that are used. The frequency of the pulse wave is between about 0.01 and 10,000 Hz, typically between 20 and 120 Hz, and is also set to the value that most significantly reduces back pain. It is understood that "Hz" refers not only to sinusoidal cycles per second but also to pulses per second in general.

The stimulation parameters must be adjusted empirically for each patient, so as to reduce the pain. Evidence for a reduction in pain may come from the testimony of the patient, from a decrease in the need for pain medication, or from a physical examination that determines painless ranges of movement on the part of the patient. Success in reducing pain may be determined within minutes or hours after the stimulation, or it may be gradual over the course of several days or weeks. Thus, there may be an acute reduction in pain, followed by a reduction of pain over the course of days or weeks that is due to adaptation of the nervous system. In preferred embodiments of the invention, the patient is allowed to turn the stimulation on or off as the need arises, and may also adjust parameters of the stimulation to optimize the therapy. The pain might be replaced with paresthesia that may be ignored by the patient. The reason that the stimulation parameters must be adjusted for each patient is related to the fact that the mechanisms responsible for the sensation of pain are complex, and they may vary from patient to patient, as now described.

The afferent nerve fibers in the lumbar posterior longitudinal ligament, the dorsal aspect of the annulus fibrosus, and the connective tissue between the posterior longitudinal ligament and annulus fibrosus are principally mechanosensitive nociceptive fibers, classified into Group III and Group IV types, with a high mechanical threshold for activation. Most are unmyelinated, and many have free nerve endings. In some studies, it is found that a superficial layer of the nerves is associated with autonomic nerves, and a deeper layer may have a purely nociceptive function. Morbid mechanical stress associated with disc abnormality and chemical stress induced by inflammation may sensitize and stimulate these nociceptive fibers in ways that are not likely under normal conditions. Such abnormal conditions may also cause growth of the nerve fibers in the direction of disc inflammation, mediated by nerve growth factor [SEKINE M, Yamashita T, Takebayashi T, Sakamoto N, Minaki Y, Ishii S. Mechanosensitive afferent units in the lumbar posterior longitudinal ligament. Spine 26(14, 2001): 1516-21; PENG B, Wu W, Hou S, Li P, Zhang C, Yang Y. The pathogenesis of discogenic low back pain. J Bone Joint Surg Br 87(1, 2005): 62-7; COPPES M H, Marani E, Thomeer R T, Groen G J. Innervation of "painful" lumbar discs. Spine 22(20, 1997):2342-9; Y. AOKI, K. Takahashi, S. Ohtori & H. Moriya: Neuropathology Of Discogenic Low Back Pain: A Review. The Internet Journal of Spine Surgery 2 (1, 2005): 1-9].

Anatomical studies show that the posterior longitudinal ligament contains an abundance of sympathetic nerve fibers that are also thought to convey pain. Posterior longitudinal ligament innervation is most abundant compared to the posterior annulus of the disc and extends beyond the level of the involved disc [EDGAR MA. The nerve supply of the lumbar intervertebral disc. J Bone Joint Surg Br 89(9, 2007):1135-9; BOGDUK N, Tynan W, Wilson A S. The nerve supply to the human lumbar intervertebral discs. J Anat 132(1, 1981):39-56; von DURING M, Fricke B, Dahlmann A. Topography and distribution of nerve fibers in the posterior longitudinal ligament of the rat: an immunocytochemical and electron-microscopical study. Cell Tissue Res 281(2, 1995):325-38; McCARTHY P W, Petts P, Hamilton A. RT97- and calcitonin gene-related peptide-like immunoreactivity in lumbar intervertebral discs and adjacent tissue from the rat. J Anat 180 (1, 1992):15-24; AHMED M, Bjurholm A, Kreicbergs A, Schultzberg M. Neuropeptide Y, tyrosine hydroxylase and vasoactive intestinal polypeptide-immunoreactive nerve fibers in the vertebral bodies, discs, dura mater, and spinal ligaments of the rat lumbar spine. Spine 18(2, 1993):268-73; KALLAKURI S, Cavanaugh J M, Blagoev D C. An immunohistochemical study of innervation of lumbar spinal dura and longitudinal ligaments. Spine 23(4, 1998):403-11; TAKEBAYASHI T, Cavanaugh J M, Kallakuri S, Chen C, Yamashita T. Sympathetic afferent units from lumbar intervertebral discs. J Bone Joint Surg Br 88(4, 2006):554-7; NAKAMURA S I, Takahashi K, Takahashi Y, Yamagata M, Moriya H. The afferent pathways of discogenic low-back pain. Evaluation of L2 spinal nerve infiltration. J Bone Joint Surg Br 78(4, 1996):606-12].

The pain signals from the posterior and posterior-lateral annulus fibrosus of the intervertebral disc, as well as the overlying posterior longitudinal ligament, are relayed to the brain via a complex network of nerves. Some of these nerves are sensory branches of the sinuvertebral nerve while others are sympathetic nerves, thus creating a dual pattern of innervation. Furthermore, the network of nerves spans regions above and below the involved disc, which likely explains the common difficulty of localizing discogenic back pain to a single vertebral level. The complexity of the nerve network is such that it is difficult to identify the circuits that are involved in the production of pain, and those circuits may in any event vary from individual to individual [J. Randy JINKINS. The anatomic and physiologic basis of local, referred, and radiating lumbosacral pain syndromes related to disease of the spine. J Neuroradiol 31 (2004): 163-180]. Compounding the complexity is the likelihood that neuropeptide pools in structures such as the dorsal root ganglion may change in response to mechanical or chemical stresses [GRONBLAD M, Weinstein J N, Santavirta S. Immunohistochemical observations on spinal tissue innervation. A review of hypothetical mechanisms of back pain. Acta Orthop Scand 62(6, 1991):614-22]. Plasticity in the components of the central and sympathetic nervous system that are involved in the sensation of pain also adds to the complexity [KUNER R. Central mechanisms of pathological pain. Nat Med 16(11, 2010):1258-66; SCHLERETH T, Birklein F. The sympathetic nervous system and pain. Neuromolecular Med 10(3, 2008):141-7].

Nevertheless, the above-cited references are consistent with at least the following mechanisms by which reversible electrical stimulation of the nerves in the posterior longitudinal ligament and underlying annulus fibrosus may reduce discogenic back pain. (1) The stimulation may cause the nerves in the posterior longitudinal ligament and/or posterior annulus fibrosus to increase the mechanical force threshold above which the nerves generate an action potential. Thus, if there are fewer nociceptive signals from these nerves, the sensation of pain may decrease. (2) The stimulation may cause the sympathetic nerves in the posterior longitudinal ligament and/or posterior annulus fibrosus to suppress the transmission of action potentials originating in the nociceptive nerves in the posterior longitudinal ligament and/or posterior annulus fibrosus. Under normal conditions, the sympathetic nervous system suppresses pain by this mechanism, and the electrical stimulation of the present invention may cause the sympathetic nerves to behave normally. On the other hand, under abnormal conditions, the sympathetic nervous system enhances the transmission of action potentials originating in nociceptive nerves. In that case, the electrical stimulation may cause a decreased enhancement by sympathetic nerves of the transmission of action potentials originating in nociceptive nerves in the posterior longitudinal ligament and/or posterior annulus fibrosus. (3) The stimulation may cause the nerves in the posterior longitudinal ligament and/or posterior annulus fibrosus to decrease their content of substance P and/or vasoactive-intestinal peptide and/or calcitonin-gene-related peptide. These chemicals are associated with inflammatory processes and pain, and their loss may reverse the inflammatory processes and pain.

For some patients, reversible stimulation of the innervation of the posterior longitudinal ligament and underlying annulus fibrosus may be unsuccessful in significantly reducing lower back pain. For those patients, the stimulator lead and any implanted pulse generator may be removed. However, before they are removed, a final attempt may be made to reduce the back pain, this time by stimulating the nerves in an attempt to produce irreversible damage to the nerves. It is understood that the term "irreversible" is not synonymous with "permanent," because once the nerves are destroyed, new nerve fibers may eventually grow back into the locations that had been occupied by the destroyed nerve fibers. Consequently, if the irreversible damage to the offending nerves is successful, it may be prudent to leave the stimulator in place for an extended period of time, in the event that newly ingrown nerves may themselves eventually need to be treated or irreversibly damaged by the devices of the invention.

As noted above in the background section, methods and devices have been proposed for irreversibly ablating nerves in the posterior longitudinal ligament, in the following patents or applications: U.S. Pat. No. 6,772,012 and U.S. Pat. No. 7,270,659, entitled Methods for electrosurgical treatment of spinal tissue, to RICART et al; U.S. Pat. No. 7,331,956, entitled Methods and apparatus for treating back pain, to HOVDA et al.; and abandoned application U.S. Ser. No. 11/105,274, corresponding to publication No. US20050261754, entitled Methods and apparatus for treating back pain, to WOLOSZKO et al. All of those methods are intended to affect the region of the posterior longitudinal ligament (among other regions) irreversibly, through the application of joule heating. The heating is due to the application of radiofrequency energy (typically 100 kHz to 2 MHz) to the offending area after applying an electrode there. Electrodes of the present invention could in principle also be used for that purpose, although it is understood that electrodes for thermal ablation are best designed specifically for that purpose [Yongmin KIM, H. Gunter Zieber, and Frank A. Yang. Uniformity of current density under stimulating electrodes. Critical Reviews in Biomedical Engineering 17(1990, 6): 585-619]. The mechanism by which the delivered radiofrequency energy heats and ablates the tissue at temperatures generally at or above 45 C is well understood [HABASH R W, Bansal R, Krewski D, Alhafid H T. Thermal therapy, part 1: an introduction to thermal therapy. Crit Rev Biomed Eng 34(6, 2006):459-89; DIEDERICH C J. Thermal ablation and high-temperature thermal therapy: overview of technology and clinical implementation. Int J Hyperthermia 21(8, 2005): 745-53; HAVEMAN J, Van Der Zee J, Wondergem J, Hoogeveen J F, Hulshof M C. Effects of hyperthermia on the peripheral nervous system: a review. Int J Hyperthermia 20(4, 2004):371-91].

However, it is possible to damage tissue by electrical stimulation mechanisms other than heating, and those are the preferred mechanisms that are used in the present invention [LEE R C, Zhang D, Hannig J. Biophysical injury mechanisms in electrical shock trauma. Annu Rev Biomed Eng 2 (2000):477-509]. In particular, nonthermal irreversible electroporation may be used to damage tissue [DAVALOS R V, Mir I L, Rubinsky B. Tissue ablation with irreversible electroporation. Ann Biomed Eng 33(2, 2005):223-31; RUBINSKY B. Irreversible electroporation in medicine. Technol Cancer Res Treat 6(4, 2007):255-60]. Because nonthermal irreversible electroporation permeabilizes and damages a cell membrane without causing thermal damage, the integrity of molecules such as collagen and elastin in the target region is generally preserved.

In electroporation, a pulse of electric field is generated between two electrodes (preferably first with one polarity, then with the reverse polarity). The damage to cells by electroporation is a function of the electric field strength, the pulse duration, and the number of pulses. To damage the cells, the field should generally be greater than 680 volts per cm (typically 1000 volts per cm), the pulse duration should be 0.5-10 millisec (typically 1.0 millisec) separated by 10 sec to minimize the likelihood of Joule heating. However, muscle and nerve cells might be damaged by electric fields as small as 60 µm, so in the present invention the electrical field is applied stepwise with increasing V/cm until the intended therapeutic effect is achieved. Damage will occur first to non-myelinated nerves, because the myelin of myelinated nerves protects those nerves [DANIELS C, Rubinsky B. Electrical field and temperature model of nonthermal irreversible electroporation in heterogeneous tissues. J Biomech Eng 131(7, 2009): 071006, pp 1-12]. However, there is an abundance of non-myelenated nerves relative to myelinated nerves in the annulus and posterior longitudinal ligament, so the nerve damage will be significant [McCARTHY P W, Petts P, Hamilton A. RT97- and calcitonin gene-related peptide-like immunoreactivity in lumbar intervertebral discs and adjacent tissue from the rat. J Anat 180 (1, 1992):15-24]. One ablative method of the present invention is to perform irreversible electroporation with relatively low electric fields to spare the myelinated nerve fibers, then resume reversible stimulation to neuromodulate their activities as in the preferred embodiment of the present invention. If the resumed reversible stimulation is not successful in reducing the back pain, then irreversible electroporation can be repeated with a higher electric field to ablate all of the offending nerves. As with the reversible stimulation, intra-operative electrophysiologic monitoring is performed in order to assure that the ablation does not harm the thecal sac and nerves contained therein [Thomas N. PAJEWSKI, Vincent Arlet and Lawrence H. Phillips. Current approach on spinal cord monitoring: the point of view of the neurologist, the anesthesiologist and the spine surgeon Eur Spine J 16(Suppl 2, 2007): 115-129; MALHOTRA, Neil R and Shaffrey, Christopher I. Intraoperative electrophysiological monitoring in spine surgery. Spine 35(25, 2010):2167-2179].

The electronics of a conventional 0 to 10V pulse generator is adapted to produce such higher voltage electroporation pulses [Abbas POURZAKI and Hossein Mirzaee. New high voltage pulse generators. Recent Patents on Electrical Engineering 2 (2009):65-76]. To irreversibly electroporate (ablate) the entire surface area covered by the lead, pulses may be generated pairwise between many of the electrodes. An advantage of limiting the electroporation pulses to pairs of electrodes within the lead is that it minimizes any pain that the patient may experience from the pulses. If two electrodes of the lead in FIG. 7A are separated by 0.5 cm, then typically a 1 millisecond pulse of 500 V is applied between them. The closer that the electrodes are to one another, then the smaller the applied voltage must be in order to damage the underlying nerve. If the parameters that are used do not reduce the pain, the pulse duration is increased, the voltage is increased (up to the limit of the pulse generator, typically 1000 V), and/or the pulsation continues every 10 seconds until the pain is reduced.

If the electroporation is not successful in significantly reducing the pain, the stimulation parameters may be changed to allow joule heating and dielectric heating of proteins to be additional mechanisms of damage. Thus, in the preferred embodiment of electroporation ablation, pulses are separated by at least 10 seconds to minimize the likelihood of damage from joule heating (i.e., a stimulation frequency of less than or equal to 0.1 Hz). This constraint may then be relaxed such that pulses are delivered at higher frequencies, with or without simultaneous adjustment of the stimulation voltage. As the frequency is increased gradually from 0.1 Hz to 10 kHz, joule heating will increasingly contribute to the mechanism of ablation, provided that the amplitude's voltage is set for a long enough time to a value greater than a voltage that may be used for reversible stimulation. Above about 10 kHz, the dielectric heating of proteins will also contribute as a mechanism of ablation, wherein cellular proteins denature and become unable to function normally. This is because at those higher stimulation frequencies, the cell membrane is no longer an effective barrier to the passage of electrical current, and capacitive coupling of power across each cell membrane permits the passage of current into the cytoplasm [LEE R C, Zhang D, Hannig J. Biophysical injury mechanisms in electrical shock trauma. Annu Rev Biomed Eng 2 (2000):477-509]. Such ablation by dielectric heating of proteins may be attempted up to the highest pulse frequency that can be generated by the pulse generator, typically 20 kHz to 50 kHz. At such frequencies, one of the lead electrodes at a time may serve as an active electrode, and current is collected in a much larger return electrode (dispersive electrode) which may comprise many of the remaining electrodes connected together electrically to the case of the pulse generator, or which may be a separate dispersive electrode if the ablation is being attempted during surgery prior to removal of the paddle lead [Yongmin KIM, H. Gunter Zieber, and Frank A. Yang. Uniformity of current density under stimulating electrodes. Critical Reviews in Biomedical Engineering 17(1990, 6): 585-619].

In order to effect a controlled thermal ablation, one or more small temperature sensor is mounted on the electrode side of the lead (e.g., thermocouple, thermistor, silicon band gap temperature sensor, resistance temperature detector or other such sensor known in the art) and connected to the pulse generator, which makes a time vs. temperature readout available to the care-giver through the programmer. A thermal dose that is effective in ablating the nerves is applied, which is a function of the measured temperature and duration of heating [HABASH R W, Bansal R, Krewski D, Alhafid H T. Thermal therapy, part 1: an introduction to thermal therapy. Crit Rev Biomed Eng 34(6, 2006):459-89; DIEDERICH C J. Thermal ablation and high-temperature thermal therapy: overview of technology and clinical implementation. Int J Hyperthermia 21(8, 2005): 745-53; HAVEMAN J, Van Der Zee J, Wondergem J, Hoogeveen J F, Hulshof M C. Effects of hyperthermia on the peripheral nervous system: a review. Int J Hyperthermia 20(4, 2004):371-91]. As with the reversible stimulation and electroporative ablation, intra-operative electrophysiologic monitoring is performed in order to assure that the thermal ablation does not harm the thecal sac and nerves contained therein. A significant difference between such thermal ablation and the methods disclosed in the above-cited patents and patent applications to RICART et al, HOVDA et al, and WOLOSZKO et al. is that in the present invention, the insulation of the lead (62 in FIG. 7) serves not only as electrical insulation, but also as thermal insulation, thus making it possible to direct accumulated applied heat to the posterior longitudinal ligament and posterior annulus fibrosus, and yet shield substantially all of the cauda equina or thecal sac from that heat. For extra thermal protection, an extra layer of thermal insulation (e.g., biocompatible ceramic foam) may be used to coat the side of the lead that is placed nearest the cauda equina.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for relieving a discogenic lumbar back pain in a patient comprising:
    positioning a plurality of electrodes within an anterior epidural space of the patient to a position adjacent to a posterior longitudinal ligament and/or a posterior annulus fibrosus;
    generating one or more electrical impulses with a pulse generator; and transmitting the electrical impulses through said electrodes to a vicinity of one or more nerves in said posterior longitudinal ligament and/or posterior annulus fibrosus; wherein the electrical impulses are configured to relieve the pain in the patient in a Step A followed by a Step B, wherein:

Step A comprises electrical stimulation of the one or more nerves, wherein no significant heat damage is generated in any tissue of the patient; wherein some of the one or more nerves are stimulated reversibly and/or are subjected to non-thermal irreversible electroporation; and wherein a determination is made that the patient finds that said stimulation without significant heat damage does not substantially relieve said pain;

and Step B comprises irreversible electrical stimulation of the one or more nerves that generates significant joule heating and/or dielectric heating of proteins; wherein all nerves within a thecal sac neighboring the anterior epidural space are substantially shielded thermally from said joule heating and/or dielectric heating; and wherein the position of the plurality of electrodes is substantially the same during Step B as the position of the plurality of electrodes during Step A.

2. The method of claim 1 wherein the plurality of electrodes is implanted within the patient.

3. The method of claim 1 wherein a first electrode, selected from among the plurality of electrodes, is configured to be an active electrode, and wherein a return or dispersive electrode is configured to comprise one or more electrodes, selected from among the plurality of electrodes excluding the first electrode.

4. The method of claim 3 wherein the plurality of electrodes is disposed linearly along one side of a shaft of electrically insulating material, and wherein any of the electrodes selected from among the plurality of electrodes may be configured to be the active electrode.

5. The method of claim 3 wherein the plurality of electrodes is disposed non-linearly or linearly along one side of a paddle of electrically insulating material, and wherein any of the electrodes selected from among the plurality of electrodes may be configured to be the active electrode.

6. The method of claim 3 wherein the plurality of electrodes is stationary, and wherein different electrodes selected from among the plurality of electrodes are sequentially configured to be the active electrode, such that the heating occurs in parts of the posterior longitudinal ligament and/or posterior annulus fibrosus that underlie the sequentially active electrodes.

7. The method of claim 1 wherein the electrical impulses are transmitted through said electrodes substantially in one direction.

8. The method of claim 7 wherein the electrical impulses are not transmitted substantially to a thecal sac or to a spinal nerve root.

9. The method of claim 4 wherein the shaft and the electrodes are configured to be positioned within the patient percutaneously.

10. The method of claim 9 wherein a cannula is inserted through a neural foramen and adjacent to the anterior epidural space; and wherein the electrodes and the shaft are inserted into a lumen of said cannula.

11. The method of claim 9 wherein the electrically insulating material is connected to one or more fins; and wherein said fins are configured to inhibit rotation of the plurality of electrodes about a longest axis of said electrically insulating shaft.

12. The method of claim 11 wherein the fins are disposed perpendicularly to a sole direction in which the electrical impulses are transmitted.

13. The method of claim 12, wherein a lead, comprising the fins, the electrically insulating shaft, and the electrodes disposed along one side of the shaft, is coated with a thermally insulating material on a side of the lead that is opposite the electrodes.

14. The method of claim 1 wherein the plurality of electrodes is disposed along a first side of an electrically insulating paddle; and wherein a length, and/or a width, and/or a perimeter of said electrically insulating material is configured to fit within a measured dimension and/or a measured surface area of one or more lumbar discs of the patient, or wherein said insulating material is configured to fit within a measured distance between two adjacent ipsilateral nerve roots of the patient.

15. The method of claim 14 wherein the electrically insulating paddle and the plurality of electrodes are positioned to a vicinity of a single intervertebral disc of the patient.

16. The method of claim 14 wherein the electrically insulating paddle and the plurality of electrodes are positioned to a vicinity of two or more intervertebral discs of the patient and/or to a vicinity of intervening vertebral bodies of said discs.

17. The method of claim 14 wherein a thermally insulating material coats a second side of the electrically insulating paddle, wherein the second side is opposite the first side.

18. The method of claim 17 wherein the thermally insulating material comprises a ceramic foam.

19. The method of claim 1 wherein the electrical impulses comprise rectangular pulses of adjustable rate, adjustable duration and adjustable amplitude for each electrode among the plurality of electrodes.

20. The method of claim 1 wherein the electrical impulses comprise pulses having a frequency of between about 10 kHz and 50 kHz.

21. The method of claim 1 wherein the heating in a vicinity of the posterior longitudinal ligament and/or the posterior annulus fibrosus is monitored using a temperature sensor.

22. The method of claim 21 wherein the temperature sensor is a thermocouple, thermistor, silicon band gap temperature sensor, or resistance temperature detector.

23. The method of claim 21 wherein a duration of heating and a temperature during heating are selected to effect a therapeutic thermal dose for the patient.

24. The method of claim 1 further comprising the performance of intra-operative electrophysiological monitoring, wherein potential damage to nerves within the thecal sac is assessed.

25. A device for relieving a discogenic lumbar back pain in a patient comprising:
a plurality of electrodes that is coupled to an electrical pulse generator; and a thermal insulator; wherein the plurality of electrodes and the thermal insulator are configured to be positioned within an anterior epidural space of the patient at a position adjacent to a posterior longitudinal ligament and/or a posterior annulus fibrosus; wherein the pulse generator is configured to transmit electrical impulses through said electrodes; wherein the electrical impulses may be configured to relieve the pain in the patient through: (A) electrical stimulation of one or more nerves within the posterior longitudinal ligament and/or the posterior annulus fibrosus, wherein some of the one or more nerves are stimulated reversibly and/or are subjected to non-thermal irreversible electroporation; and wherein no significant heat damage is generated in any tissue of the patient; and in an alternate selectable configuration of the electrical impulses, through: (B) irreversible electrical stimulation of the one or more nerves that generates significant joule heating and/or dielectric heating of proteins; wherein the thermal insulator is configured to cover a thecal sac such that all nerves within said thecal sac are substantially shielded from said joule and/or dielectric heating; and wherein electrical impulse configurations (A) and (B) are configured for use when the plurality of electrodes resides in a stationary position within the anterior epidural space of the patient.

26. The device of claim 25 wherein the electrodes are configured to be implanted within the patient.

27. The device of claim 25 wherein a first electrode selected from among the plurality of electrodes may be configured to be an active electrode, and wherein a return or dispersive electrode may be configured to comprise one or more electrodes selected from among the plurality of electrodes excluding the first electrode.

28. The device of claim 27 wherein the plurality of electrodes is disposed linearly along one side of a shaft of electrically insulating material, and wherein any of the electrodes among the plurality of electrodes may be configured to be the active electrode.

29. The device of claim 27 wherein the plurality of electrodes is disposed non-linearly or linearly along one side of a paddle of electrically insulating material, and wherein any of the electrodes among the plurality of electrodes may be configured to be the active electrode.

30. The device of claim 25 wherein the electrical impulses are configured to be transmitted through the electrodes substantially in one direction.

31. The device of claim 28 wherein the shaft and the electrodes are configured to be positioned within the patient percutaneously.

32. The device of claim 31 further comprising a cannula, wherein the electrodes and the shaft are configured to be inserted into a lumen of said cannula.

33. The device of claim 31 wherein the electrically insulating shaft is connected to one or more fins; and wherein said fins are configured to inhibit rotation of the plurality of electrodes about a longest axis of said electrically insulating shaft when said shaft is positioned within the anterior epidural space of the patient.

34. The device of claim 33 wherein the fins are disposed perpendicularly to a sole direction in which the electrical impulses are configured to be transmitted.

35. The device of claim 25 wherein the plurality of electrodes is disposed nonlinearly or linearly along a first side of an electrically insulating paddle; and wherein a length, and/or a width, and/or a perimeter of said electrically insulating material is configured to fit within a measured dimension and/or a measured surface area of one or more lumbar discs of the patient, or wherein said insulating material is configured to fit within a measured distance between two adjacent ipsilateral nerve roots of the patient.

36. The device of claim 35 wherein a thermally insulating material is disposed along a second side of the electrically insulating paddle, wherein the second side is opposite the first side.

37. The device of claim 36 wherein the thermally insulating material comprises a ceramic foam.

38. The device of claim 25 wherein the electrical impulses are configured to comprise rectangular pulses of adjustable rate, adjustable duration and adjustable amplitude for each electrode among the plurality of electrodes.

39. The device of claim 25 wherein the electrical impulses are configured to have a frequency of between about 10 kHz and 50 kHz.

40. The device of claim 25 further comprising a temperature sensor.

41. The device of claim 40 wherein the temperature sensor is a thermocouple, thermistor, silicon band gap temperature sensor, or resistance temperature detector.

42. The device of claim 25, and further comprising a trocar, or a guide wire, or a stylet, or an introducer cannula, or an obturator, or a lead blank; wherein the trocor, or the guide wire, or the stylet, or the introducer cannula, or the obturator, or the lead blank is configured for the placement into the patient of the device of claim 25.

43. A device for relieving a discogenic lumbar back pain in a patient comprising:
a plurality of electrodes that is coupled to an electrical pulse generator; and a thermal insulator; wherein the plurality of electrodes and the thermal insulator are configured to be implanted within an anterior epidural space of the patient at a fixed position adjacent to a posterior longitudinal ligament and/or a posterior annulus fibrosus; wherein the pulse generator is configured to transmit electrical impulses through said electrodes; wherein said electrical impulses are configured to relieve the pain in the patient through electrical stimulation in the vicinity of one or more nerves in said posterior longitudinal ligament and/or said posterior annulus fibrosus; wherein said electrical impulses generate therapeutically significant joule heating and/or dielectric heating of proteins; wherein a selectable electrode among the plurality of electrodes may be configured to be an active electrode, and wherein a return or dispersive electrode may be configured to comprise one or more electrodes selected from among the plurality of electrodes excluding the active electrode; and wherein the thermal insulator is configured to cover a thecal sac such that all nerves within said thecal sac are shielded to prevent an iatrogenesis that would arise from heating of said thecal sac.

* * * * *